(12) United States Patent
Haudenschild et al.

(10) Patent No.: US 9,133,259 B2
(45) Date of Patent: Sep. 15, 2015

(54) CARTILAGE OLIGOMERIC MATRIX PROTEIN (COMP)—GROWTH FACTOR COMPLEXES AND USES THEREOF

(75) Inventors: Dominik Haudenschild, Davis, CA (US); Paul Di Cesare, Sacramento, CA (US); Jasper Yik, Elk Grove, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/879,399

(22) PCT Filed: Sep. 14, 2011

(86) PCT No.: PCT/US2011/051610
§ 371 (c)(1),
(2), (4) Date: Aug. 12, 2013

(87) PCT Pub. No.: WO2012/050714
PCT Pub. Date: Apr. 19, 2012

(65) Prior Publication Data
US 2013/0315889 A1     Nov. 28, 2013

Related U.S. Application Data

(60) Provisional application No. 61/393,850, filed on Oct. 15, 2010.

(51) Int. Cl.
| | | |
|---|---|---|
| *A61K 38/00* | (2006.01) | |
| *A61K 38/16* | (2006.01) | |
| *A61K 38/17* | (2006.01) | |
| *A61K 38/18* | (2006.01) | |
| *C07K 14/00* | (2006.01) | |
| *C07K 14/435* | (2006.01) | |
| *C07K 14/475* | (2006.01) | |
| *C07K 14/495* | (2006.01) | |
| *C07K 14/51* | (2006.01) | |
| *C07K 14/485* | (2006.01) | |
| *C07K 14/78* | (2006.01) | |
| *A61L 27/22* | (2006.01) | |
| *A61L 27/38* | (2006.01) | |

(Continued)

(52) U.S. Cl.
CPC .............. *C07K 14/485* (2013.01); *A61L 27/227* (2013.01); *A61L 27/3817* (2013.01); *A61L 27/3821* (2013.01); *A61L 27/3834* (2013.01); *A61L 27/54* (2013.01); *A61L 27/58* (2013.01); *C07K 14/475* (2013.01); *C07K 14/495* (2013.01); *C07K 14/51* (2013.01); *C07K 14/78* (2013.01); *A61K 38/179* (2013.01); *A61L 2430/02* (2013.01); *A61L 2430/06* (2013.01); *A61L 2430/38* (2013.01)

(58) Field of Classification Search
None
See application file for complete search history.

(56) References Cited

U.S. PATENT DOCUMENTS

2009/0170959 A1*    7/2009   Montclare et al. ............ 514/773

OTHER PUBLICATIONS

Darling, E., et al., "Growth factor impact on articular cartilage subpopulations," *Cell and Tissue Research*, vol. 322(3), pp. 463-473 (Dec. 2005).

(Continued)

*Primary Examiner* — Elizabeth C Kemmerer
(74) *Attorney, Agent, or Firm* — Kilpatrick Townsend & Stockton LLP

(57) ABSTRACT

The present invention relates to protein complexes or scaffold comprising cartilage oligomeric matrix protein (COMP) polypeptides bound to one or more growth factors, and methods of their use in promoting chondrogenesis and/or osteogenesis, and repair of cartilage and bone lesions.

43 Claims, 19 Drawing Sheets

(51) Int. Cl.
*A61L 27/54* (2006.01)
*A61L 27/58* (2006.01)

(56) References Cited

OTHER PUBLICATIONS

Oldberg, A., et al., "COMP (cartilage oligomeric matrix protein) is structurally related to the thrombospondins," *Journal of Biological Chemistry*, vol. 267(31), pp. 22346-22350 (Nov. 5, 1992).
Olney, R., et al., "Growth factor regulation of human growth plate chondrocyte proliferation in vitro," *Biochemical and Biophysical Research Communications*, vol. 317(4), pp. 1171-1182 (May 14, 2004).
Sampath, T., et al., "Bovine osteogenic protein is composed of dimers of OP-1 and BMP-2A, two members of the transforming growth factor-beta superfamily," *Journal of Biological Chemistry*, vol. 265(22), pp. 13198-13205 (Aug. 5, 1990).
Xu, K., et al., "Cartilage oligomeric matrix protein associates with granulin-epithelin precursor (GEP) and potentiates GEP-stimulated chondrocyte proliferation," *Journal of Biological Chemistry*, vol. 282(15), pp. 11347-11355 (Apr. 13, 2007).

* cited by examiner

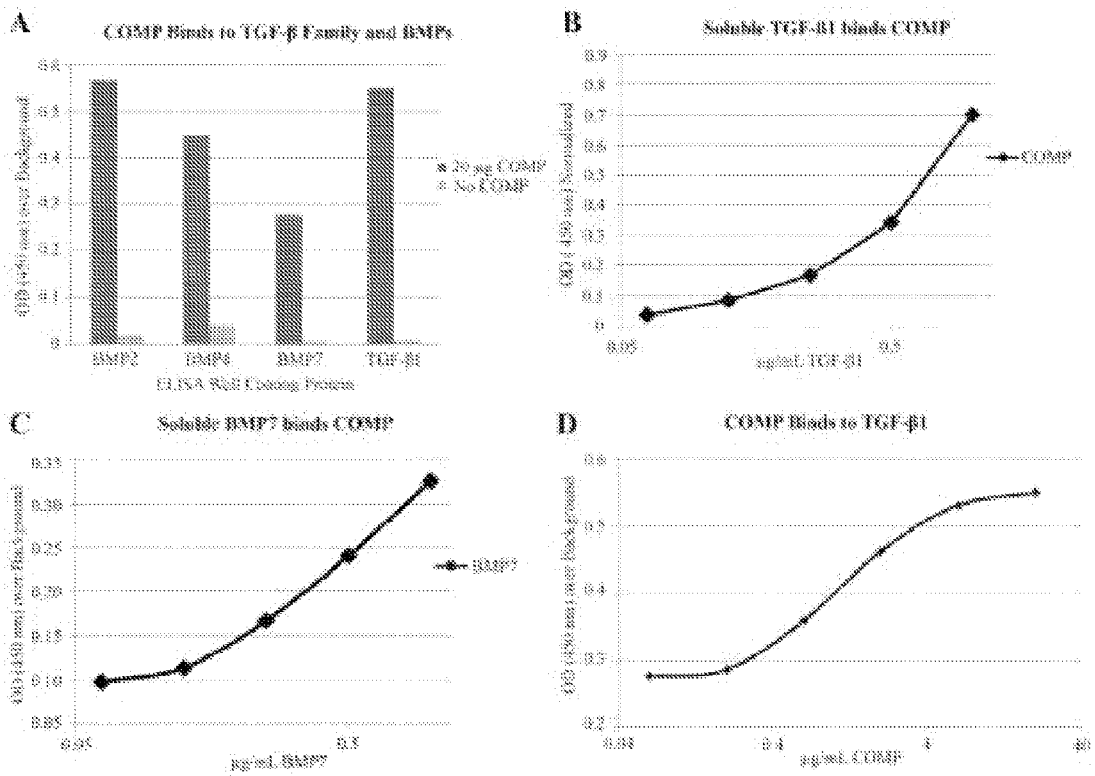
Fig. 2A-D

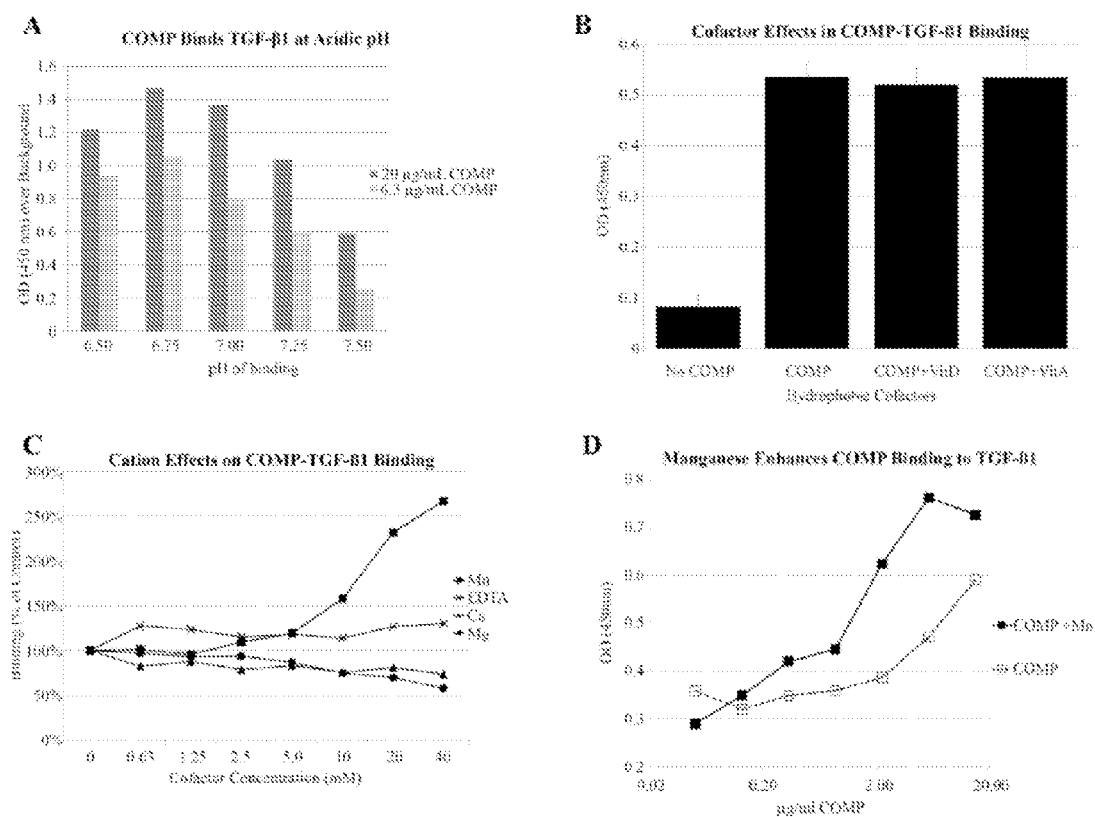
Fig. 3A-D

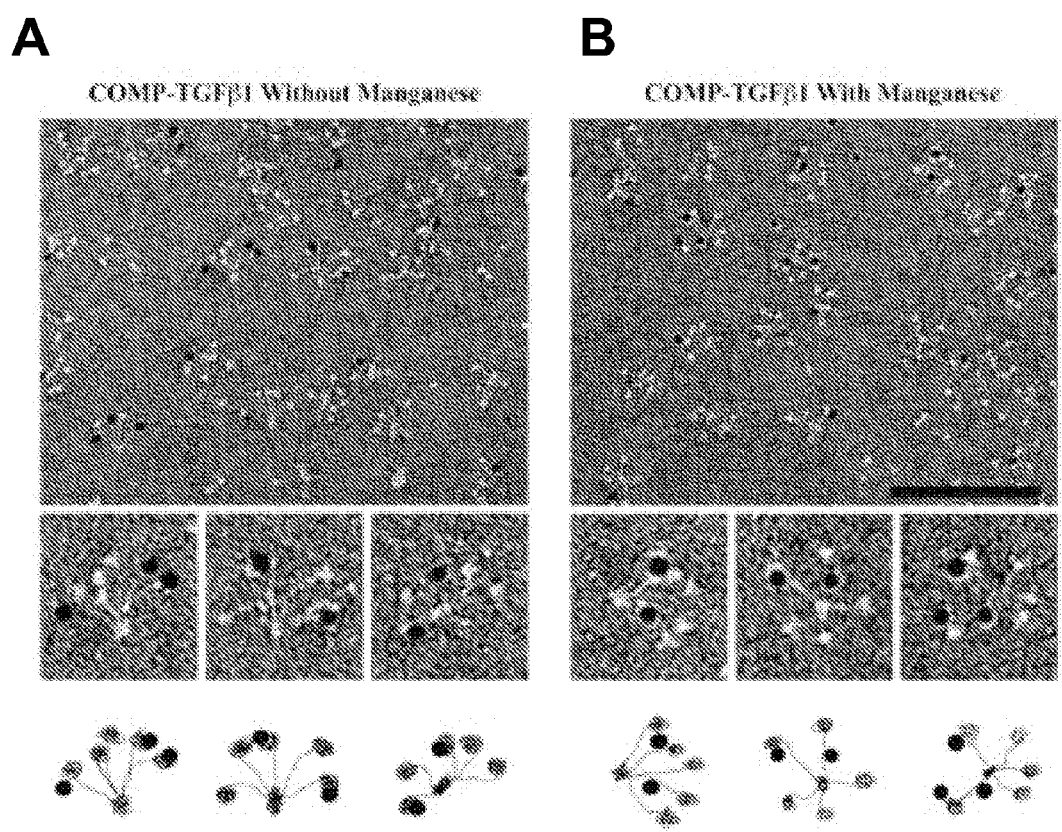
Fig. 4A-B

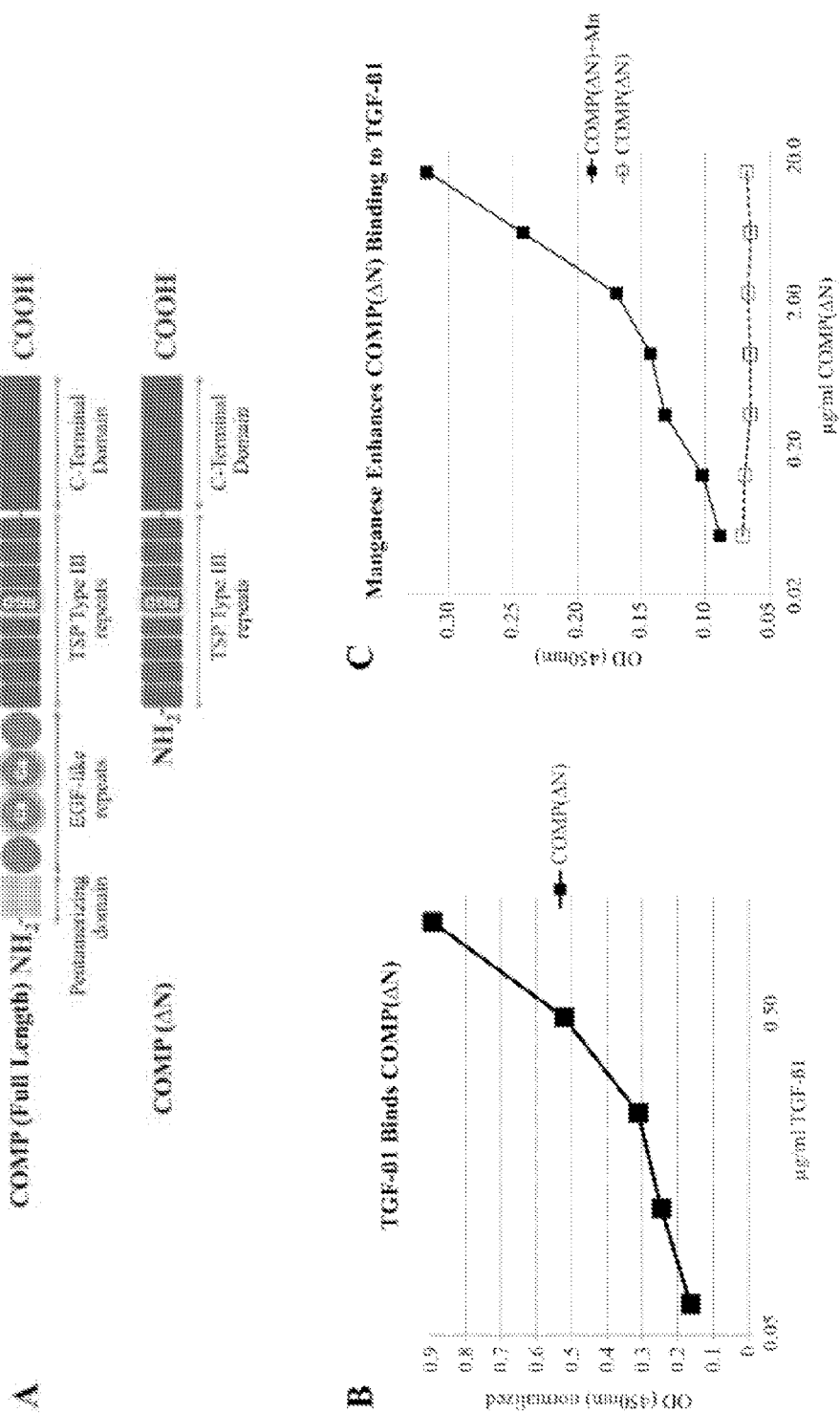
Fig. 5A-C

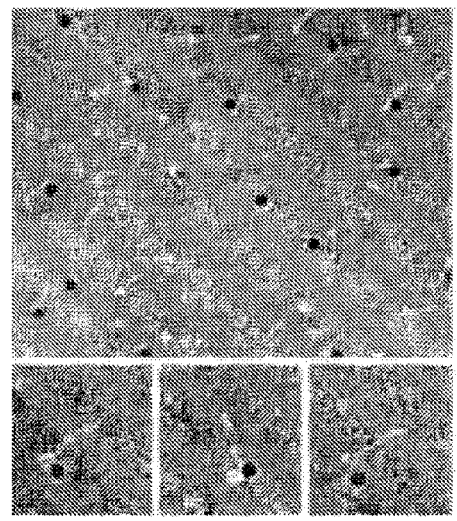
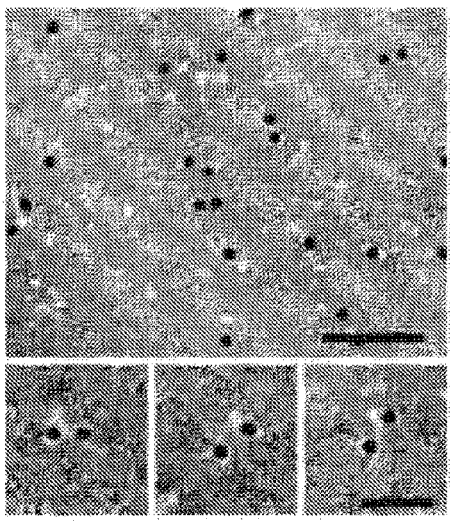
COMP(ΔN)-TGFβI Without Magnanese | COMP(ΔN)-TGFβI With Magnanese
*Fig. 6A*        *Fig. 6B*

*Fig. 8A-B*

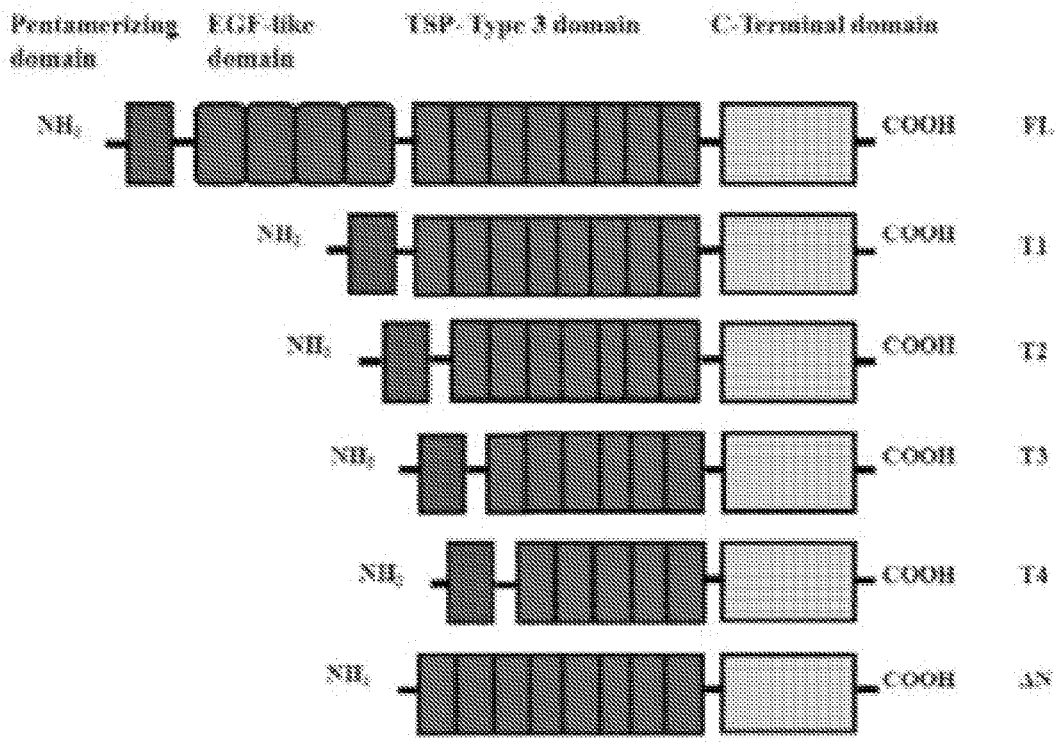
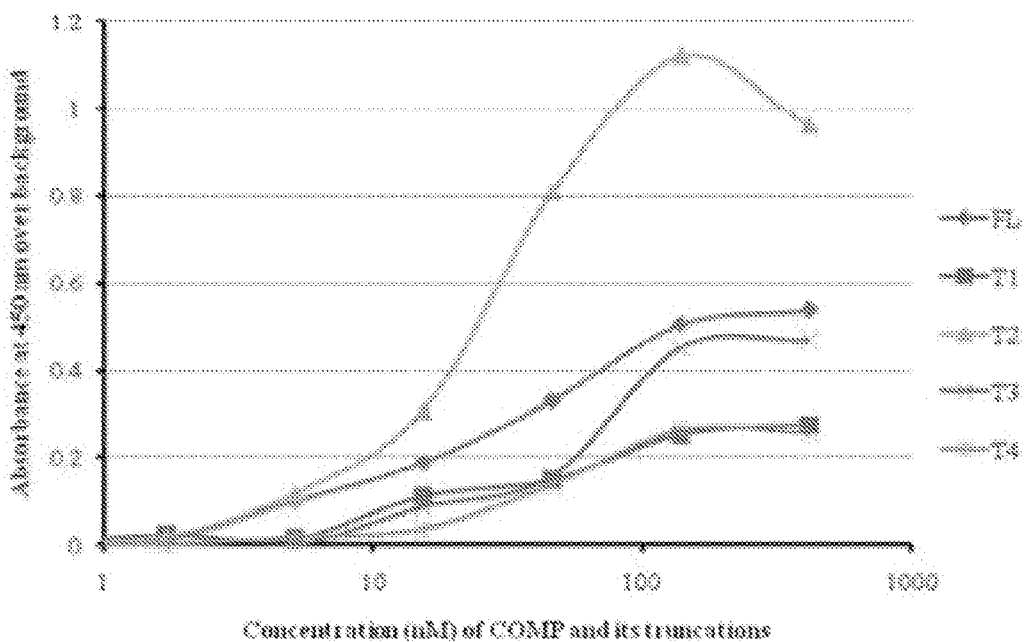
Fig. 10A-B

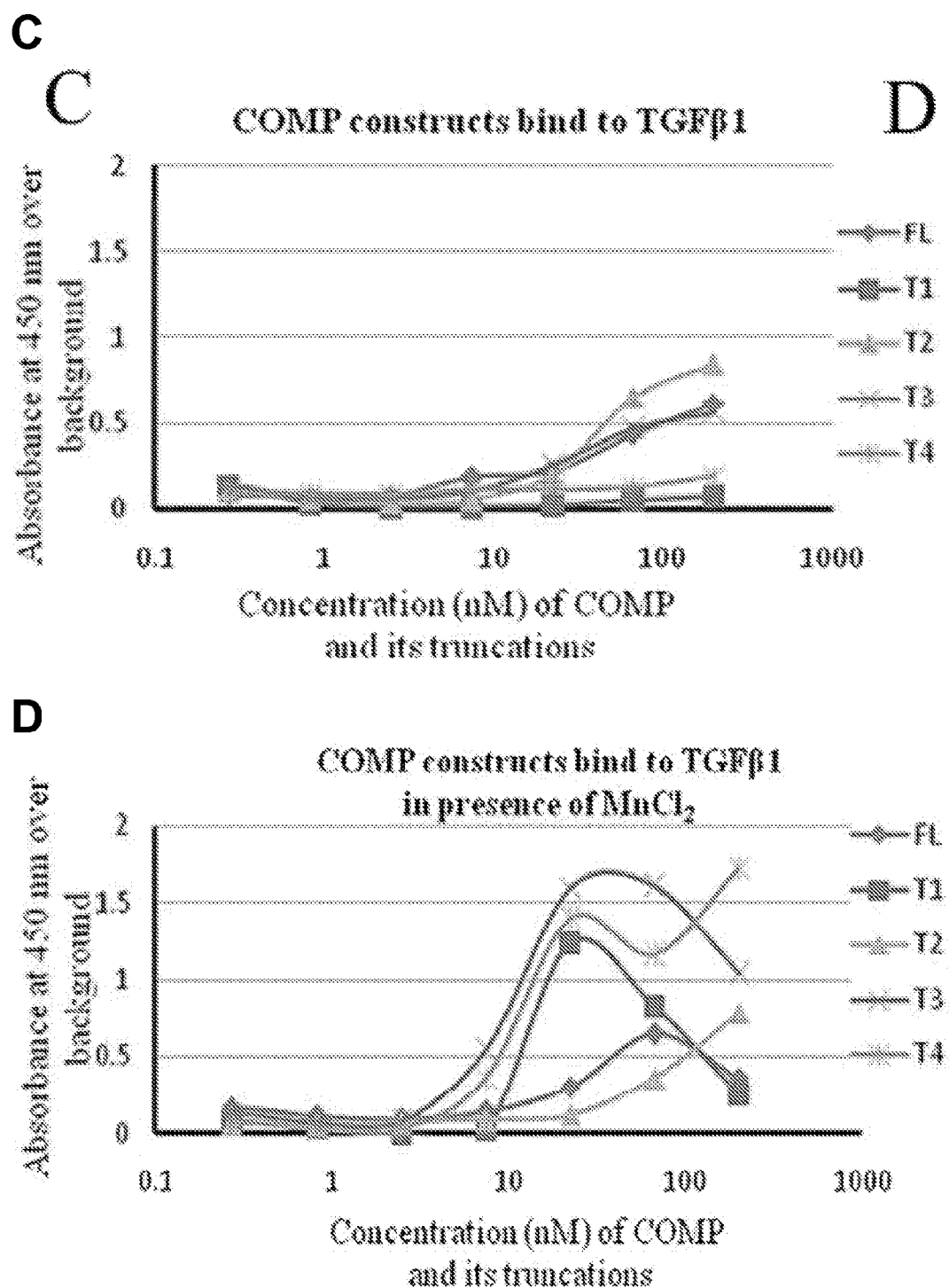
Fig. 10C-D

BMPR2

1day

130kda

BMP-2: 100ng/mL    −    +    −    +
COMP: 200ng/mL    −    −    +    +

CARTILAGE OLIGOMERIC MATRIX PROTEIN (COMP)—GROWTH FACTOR COMPLEXES AND USES THEREOF

CROSS-REFERENCE TO RELATED APPLICATIONS

This application is a U.S. National Phase of PCT/US2011/051610, filed Sep. 14, 2011, which claims the benefit of U.S. Provisional Application No. 61/393,850, filed on Oct. 15, 2010, which are hereby incorporated herein by reference in their entirety for all purposes.

FIELD OF THE INVENTION

The present invention relates to protein complexes or scaffold comprising cartilage oligomeric matrix protein (COMP) polypeptides bound to one or more growth factors, and methods of their use in promoting chondrogenesis and/or osteogenesis, and repair of cartilage and bone lesions.

BACKGROUND OF THE INVENTION

The human and financial impacts of osteoarthritis (OA) in the United States are immense. Regardless of the original cause, OA directly impacts the quality of life of nearly 21 million people in the US and is second only to cardiovascular disease in producing chronic disability [Altman and Moskowitz (1998) *J Rheumatol* 25, 2203-2212]. The world health organization estimates that OA accounts for 25% of visits to primary care physicians. The total cost of arthritis and other rheumatic conditions in 2003 were $128 billion—equivalent to 1.2% of the US gross domestic product [Morb Mortal Wkly Rep (2006) 55:1089-1092; Morb Mortal Wkly Rep (2007) 56:4-7]. Costs are rising substantially, with the estimated number of adults affected by OA reaching 59 million by 2020 [Lawrence, et al., *Arthritis Rheum* (1998) 41, 778-799]. Despite the tremendous burden of osteoarthritis in our society, it remains an incurable disease. There is currently no optimal solution for the clinical problem of the pre-arthritic condition of joint injury or degradation that will lead to future osteoarthritis. Treatments of osteoarthritis are designed to address the pain symptoms associated with OA, and no option offers treatment of the underlying pathology or improvements in the function of the deteriorating cartilage and bone.

Cartilage tissue engineering is a promising treatment for arthritic joints. Cartilage can be formed in-vitro from mesenchymal stem cells induced by the proper combination of growth factors. TGF-β1, which was originally identified as "cartilage-inducing factor" [Seyedin, et al., *J Biol Chem* (1986) 261, 5693-5695], is a potent inducer of cartilage formation in stem cells and is commonly used in cartilage tissue engineering. TGF-β1 stabilizes the chondrocyte phenotype, initially by promoting chondrogenesis in stem cells, and later by preventing hypertrophy. TGF-β1 also has potent anti-inflammatory effects in joints by counteracting the pro-inflammatory interleukin-1 pathways. Expression of TGF-β1 is reduced in OA, and local delivery of TGF-β1 is effective in stimulating cartilage repair in animal models of osteoarthritis and traumatic injury (reviewed in Grimaud, et al., *Cytokine Growth Factor Rev* (2002) 13, 241-257).

The Transforming Growth Factor beta (TGF-β1) family is a group of potent growth factors that increase chondrogenesis both in stem cells and in de-differentiated chondrocytes. The chondrogenic effects of TGF-β are widely used for tissue engineering of cartilaginous constructs. TGF-β activity is tightly regulated by many extracellular factors that control its bioavailability, most often through interfering with the binding of TGF-β1 to its receptors [Derynck and Miyazono, 2007. "The TGF-β family." Cold Spring Harbor Laboratory Press, Cold Spring Harbor, N.Y].

Cartilage Oligomeric Matrix Protein (COMP) is an important cartilage protein that is essential for the structural integrity of the cartilage extracellular matrix. COMP binds to matrix components including collagens [Blumbach, et al., *Matrix Biol* (2008) 27, 306-318], aggrecan [Chen, et al., *J Biol Chem* (2007) 282, 24591-24598], matrilin [Mann, et al., *J Biol Chem.* (2004) 279(24):25294-8], fibronectin [Di Cesare, et al., *Matrix Biol* (2002) 21:461-470], and extracellular matrix protein-1 (ECM-1) [Kong, et al, *Matrix Biol* (2010) 29, 276-286]. Mature cartilage oligomeric matrix protein (COMP) is a large (524-kDa) disulfide-bonded homopentameric glycoprotein located mainly in the extracellular matrix of joint tissues such as cartilage, ligament, tendon and synovium (Hedbom, et al., (1992) *J Biol Chem* 267, 6132-6136; Newton, et al., (1994) *Genomics* 24, 435-439; Oldberg, et al., (1992) *J Biol Chem* 267, 22346-22350; and Morgelin, et al., (1992) *J Biol Chem* 267, 6137-6141). Each COMP monomer consists of an N-terminal coiled-coil domain, 4 EGF repeats, 8 TSP-3 repeats, and a thrombospondin C-terminal domain. The N-terminal coiled coil domain is responsible for forming the pentameric mature COMP protein, and contains two cysteine residues that covalently link adjacent chains (Efimov, et al., (1996) *Proteins* 24, 259-262; Malashkevich, et al., (1996) *Science* 274, 761-765; and Malashkevich, et al., (1996) *Science* 274, 761-765). The hydrophobic core formed by the coiled coil domains in COMP pentamers can bind small molecules such as retinol and vitamin-D (Ozbek, et al., (2002) *EMBO J* 21, 5960-5968). COMP has 4 EGF repeats, 13 TSP type 3 repeats, and a thrombospondin C-terminal domain (CTD), which together are responsible for binding interactions with other proteins and extracellular matrix components (Tan, et al., (2009) *FASEB J* 23, 2490-2501). Calcium-binding sites are located throughout COMP. Two of the four EGF repeats have calcium-binding sites, as do all of the TSP-3 repeats and the CTD. Calcium, and presumably other cations as well, alters the conformation of COMP and affects the binding interactions between COMP and other proteins.

COMP interacts with multiple other cartilage matrix components, including collagens type I, II and IX (Blumbach, et al., (2008) *Matrix Biol* 27, 306-318), proteoglycans such as aggrecan (Chen, et al., (2007) *J Biol Chem* 282, 24591-24598), non-collagenous matrix proteins such as fibronectin (Di Cesare, et al., (2002) *Matrix Biol* 21, 461-470) and matrilins (Mann, et al., *J Biol Chem.* (2004) 279(24):25294-8), as well as to glycosaminoglycans and heparin (Chen, et al., (2007) J Biol Chem 282, 24591-24598; DiCesare, et al., (1994) *Eur J Biochem* 223, 927-937). The repeated modular structure of COMP is critically important for its function as a 'bridge' that assembles multiple extracellular matrix components (Tan, et al., (2009) *FASEB J* 23, 2490-2501). For example, the COMP pentamer (but not monomeric COMP) simultaneously binds several free collagen molecules to accelerate collagen fibrillogenesis (Budde, et al., (2005) *Mol Cell Biol* 25, 10465-10478). In addition to binding extracellular proteins, COMP also contains an integrin-binding RGD sequence (Tan, et al., (2009) FASEB J 23, 2490-2501; Chen, et al., (2005) *J Biol Chem* 280, 32655-32661; Wang, et al., (2010) *Circ Res* 106, 514-525), and it can interact with the thrombospondin receptor CD47 (Rock, et al., (2010) *Mol Cell Biochem* 338, 215-224). The full implications of these cell-surface interactions in cartilage formation have not been discovered.

The expression of COMP is detected early in chondrogenic differentiation during embryonic skeletogenesis (Franzen, et al., (1987) *Differentiation* 36, 199-210). In the adult, COMP continues to be expressed in joint tissues, primarily in cartilage but also at detectable levels in ligaments, tendons, and synovium (Koelling, et al., (2006) *Arthritis Res Ther* 8, R56). COMP is expressed in isolated chondrocytes, but it is rapidly down-regulated during monolayer expansion of chondrocytes. This down-regulation is reversible, as it is rapidly re-expressed during chondrogenic redifferentiation (Zaucke, et al., (2001) *Biochem J* 358, 17-24). Our recent results suggest that COMP expression is also an early marker of the stem cell commitment to the chondrogenic lineage (Li, et al., (2011) *Osteoarthritis and cartilage/OARS, Osteoarthritis Research Society*).

The biological processes during which COMP expression is induced, including in vitro chondrogenic differentiation of stem cells and redifferentiation of passaged chondrocytes, are all heavily dependent on TGF-β signaling (Joyce, et al., (1990) *J Cell Biol* 110, 2195-2207; and Kawamura, et al., (1988) *Dev Biol* 130, 435-442). This suggests that there may be an interaction between COMP and TGF-β. Indeed TGF-β upregulates COMP mRNA expression and protein production in many systems (Recklies, et al., (1998) *Arthritis Rheum* 41, 997-1006; Barry, et al., (2001) *Exp Cell Res* 268, 189-200). However, a direct interaction between COMP and TGF-β proteins has not yet been identified. The binding of COMP to cell surface proteins and transmembrane receptors raises the intriguing possibility that, if COMP were able to directly bind to growth factors, it could act as a scaffold and influence the presentation of the growth factors to the receptors. Due to its repeated modular structure, COMP may bind several growth factors and increase their local concentration at the cell surface to enhance signaling.

SUMMARY OF THE INVENTION

The present invention provides isolated protein complexes or protein scaffolds comprising one or more monomers of cartilage oligomeric matrix protein (COMP) bound to one or more growth factors, wherein the one or more monomers of COMP comprise a growth factor binding domain. Usually, the COMP monomers comprise at least one of a thrombospondin-3 (TSP-3) domain and a COMP domain. In some embodiments, the COMP monomers comprise a C-terminal COMP domain, e.g., amino acid residues 529-757 or 527-757 of SEQ ID NO:1. In some embodiments, the COMP monomers comprise a thrombospondin-3 (TSP-3) domain and a COMP domain. In some embodiments, the COMP monomers comprise one or more C-terminal COMP domains and one or more epidermal growth factor (EGF)-like domains. In some embodiments, the COMP monomers comprise one or more C-terminal COMP domains, one or more thrombospondin-3 (TSP-3) domains and one or more epidermal growth factor (EGF)-like domains. The one or more monomers of COMP can be full length polypeptides or fragments thereof.

In some embodiments, the protein complex or protein scaffold comprises 2, 3, 4, 5 or more monomers of COMP. In some embodiments, the protein complex or protein scaffold comprises a COMP pentamer, i.e., five monomers of COMP.

In some embodiments, the monomers of COMP are fragments of full-length COMP polypeptide. In some embodiments, the monomers of COMP do not comprise one or more domains selected from the group consisting of an N-terminal oligomerization domain and an epidermal growth factor (EGF)-like domain. In some embodiments, the N-terminal oligomerization domain (i.e., pentamerization domain) is deleted. In some embodiments, one, two, three or four of the epidermal growth factor (EGF)-like domains are deleted. In some embodiments, one or more, e.g., one, two, three or four of the TSP_3 repeats are deleted. In some embodiments, the monomers of COMP comprise one or more domains selected from the group consisting of an N-terminal oligomerization domain and an epidermal growth factor (EGF)-like domain. In some embodiments, the monomers of COMP do not comprise either an N-terminal oligomerization domain or an epidermal growth factor (EGF)-like domain.

The stoichiometry of the growth factors can be at least 1:1 growth factor polypeptides bound for every COMP monomer. In some embodiments, the stoichiometry of the growth factors can be at least 1.5:1 or 2:1 growth factor polypeptides bound for every COMP monomer. In some embodiments, at least two growth factor polypeptides are bound to one COMP monomer. The growth factors bound to the COMP protein scaffold or protein complex can be the same or different.

In some embodiments, the one or more growth factors are a member of the transforming growth factor-beta 1 (TGF-β1) superfamily. In some embodiments, the one or more growth factors are selected from the group consisting of TGF-β1, bone morphogenetic protein (BMP)-2, BMP-3, BMP-4, BMP-5, BMP-6 and BMP-7. In some embodiments, the one or more growth factors are selected from the group consisting of TGF-β1, bone morphogenetic protein (BMP)-2, BMP-4 and BMP-7. In some embodiments, the one or more growth factors are selected from the group consisting of TGF-β1, BMP-2, BMP-3, BMP-4, BMP-5, BMP-6, BMP-7, fibroblast growth factor-2 (FGF-2), hepatic growth factor (HGF), vascular endothelial growth factor (VEGF) and insulin-like growth factor 1 (IGF-1).

In some embodiments, the COMP-growth factor protein complexes or protein scaffolds are comprised within a matrix. As appropriate or desired, the matrix can be bioresorbable or biodegradable. As appropriate or desired, the matrix can be configured as a sheet or as a bone graft. For example, the matrix comprising the COMP-growth factor protein complexes or protein scaffolds can be formulated for use as an autogenous graft, an allograft, a demineralized bone matrix, or a synthetic bone graft substitute.

In some embodiments, the matrix further comprises one or more materials selected from the group consisting of treated cartilage and bone matrices, collagens, hyaluronan, fibrin gels, carbon fibers, porous polylactic acid, type I collagen gel, and type II collagen gel. In some embodiments, the matrix further comprises one or more bone matrix proteins selected from the group consisting of, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin.

In a further aspect, the invention provides methods for repairing a cartilage lesion, comprising implanting into the cartilage lesion a COMP-growth factor protein complex or protein scaffold, within or without a matrix, as described herein, wherein the COMP-growth factor complex in the protein complex, protein scaffold or matrix promotes chondrogenesis, thereby repairing the cartilage lesion.

In some embodiments, the cartilage lesion is an articular cartilage lesion. In some embodiments, the cartilage lesion is a meniscal cartilage lesion.

In a related aspect, the invention provides methods of promoting bone growth at a bone lesion, comprising contacting the bone lesion with or implanting into the bone lesion a COMP-growth factor protein complex or protein scaffold, within or without a matrix, as described herein, wherein the COMP-growth factor complex in the protein complex, protein scaffold or matrix promotes bone growth, thereby promoting osteogenesis or bone growth at the bone lesion. In some embodiments, the COMP-growth factor protein complex or protein scaffold is comprised in a matrix formulated for use as a bone graft. In some embodiments, the bone lesion is a bone fracture. In some embodiments, the bone lesion is a spinal fusion site.

In another aspect, the invention of promoting chondrogenesis, comprising contacting a cell capable of producing cartilage with a COMP-growth factor protein complex or protein scaffold, within or without a matrix, as described herein. In some embodiments, the cell is a chondrocyte. In some embodiments, the cell is a stem cell, for example a multipotent, pluripotent, or induced pluripotent stem cell. In some embodiments, the stem cell is a mesenchymal stem cell or a bone marrow stem cell. In various embodiments of methods for promoting chondrogenesis, the COMP-growth factor complex/scaffold comprises one or more TGF-β1 polypeptides.

In another aspect, the invention of promoting osteogenesis, comprising contacting a cell capable of producing bone with a COMP-growth factor protein complex or protein scaffold, within or without a matrix, as described herein. In some embodiments, the cell is an osteoblast or an osteogenic cell. In some embodiments, the cell is a stem cell, for example a multipotent, pluripotent, or induced pluripotent stem cell. In some embodiments, the stem cell is a mesenchymal stem cell or a bone marrow stem cell. In some embodiments, the stem cell is an osteoprogenitor cell, an osteoblast or an osteogenic cell. The cell capable of producing bone can be in vivo or in vitro. In various embodiments of methods for promoting osteogenesis, the COMP-growth factor complex/scaffold comprises one or more BMP polypeptides, e.g., BMP-2, BMP-3, BMP-4, BMP-5, BMP-6 and BMP-7.

In a further aspect, the invention provides methods of delivering one or more growth factors to a target cell, comprising contacting the target cell with a COMP-growth factor protein complex or protein scaffold, within or without a matrix, as described herein. The target cell capable of producing cartilage can be in vivo or in vitro. In some embodiments, the target cell is a chondrocyte. In some embodiments, the target cell is an osteoprogenitor cell, an osteoblast or an osteogenic cell. In some embodiments, the target cell is an epidermal cell or a skin cell. In some embodiments, the target cell expresses Integrins β3, α5, αvβ3, CD47 Receptor, ADAMTS7 or ADAMTS12. In some embodiments, the target cell is in a subject and the protein complex or protein scaffold is administered to the subject.

DEFINITIONS

The term "Cartilage Oligomeric Matrix Protein" or "COMP" refers to a noncollagenous extracellular matrix (ECM) protein comprises of five identical glycoprotein subunit monomers, each monomer with EGF-like and calcium-binding (thrombospondin-like) domains. Oligomerization results from formation of a five-stranded coiled coil and disulfides. Structurally, "Cartilage Oligomeric Matrix Protein" or "COMP" refers to nucleic acids and polypeptide polymorphic variants, alleles, mutants, and interspecies homologs that: (1) have an amino acid sequence that has greater than about 90% amino acid sequence identity, for example, 91%, 92%, 93%, 94%, 95%, 96%, 97%, 98% or 99% or greater amino acid sequence identity, preferably over a region of at least about 25, 50, 100, 200, 400, or more amino acids, or over the full-length, to an amino acid sequence encoded by a COMP nucleic acid (see, e.g., GenBank Accession No. NM_000095.2); (2) bind to antibodies, e.g., polyclonal antibodies, raised against an immunogen comprising an amino acid sequence of a COMP polypeptide (e.g., GenBank Accession No. NP_000086.2); or an amino acid sequence encoded by a COMP nucleic acid (e.g., COMP polynucleotides described herein), and conservatively modified variants thereof; (3) specifically hybridize under stringent hybridization conditions to an anti-sense strand corresponding to a nucleic acid sequence encoding a COMP protein, and conservatively modified variants thereof; (4) have a nucleic acid sequence that has greater than about 90%, preferably greater than about 91%, 92%, 93%, 94%, 95%, 96%, 97%, 98%, 99%, or higher nucleotide sequence identity, preferably over a region of at least about 25, 50, 100, 200, 500, 1000, 2000 or more nucleotides, or over the full-length, to a COMP nucleic acid (e.g., COMP polynucleotides, as described herein, and COMP polynucleotides that encode COMP polypeptides, as described herein). Based on the knowledge of COMP homologs, those of skill can readily determine residue positions that are more tolerant to substitution. For example, amino acid residues conserved amongst species are less tolerant of substitution or deletion. Similarly, amino acid residues that are not conserved amongst species are more tolerant of substitution or deletion, while retaining the function of the COMP protein.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine I, Lysine (K);
5) Isoleucine (I), Leucine (L), Methionine (M), Valine (V);
6) Phenylalanine (F), Tyrosine (Y), Tryptophan (W); and
7) Serine (S), Threonine (T)
(see, e.g., Creighton, Proteins (1984)).

The term "monomer" with respect to a COMP protein refers to a polypeptide of one COMP glycoprotein subunits. The monomer can be a full-length polypeptide or a fragment thereof.

The terms "identical" or percent "identity," and variants thereof in the context of two or more polypeptide sequences, refer to two or more sequences or subsequences that are the same. Sequences are "substantially identical" if they have a specified percentage of amino acid residues or nucleotides that are the same (i.e., at least 60% identity, optionally at least 65%, 70%, 75%, 80%, 85%, 90%, 95%, 96%, 97%, 98%, or 99% identity over a specified region (or the whole reference sequence when not specified)), when compared and aligned for maximum correspondence over a comparison window, or designated region as measured using one of the following sequence comparison algorithms or by manual alignment and visual inspection. The present invention provides polypeptides substantially identical to COMP and the growth factors described herein. Optionally, the identity exists over a region that is at least about 50 amino acids in length, or more preferably over a region that is 100 to 500 or 1000 or more amino acids in length, or over the full-length of the sequence.

The terms "similarity," or "percent similarity," and variants thereof in the context of two or more polypeptide sequences, refer to two or more sequences or subsequences that have a specified percentage of amino acid residues that are either the same or similar as defined in the 8 conservative amino acid substitutions defined above (i.e., 60%, optionally 65%, 70%, 75%, 80%, 85%, 90%, 95%, 96%, 97%, 98% or 99% similar over a specified region), when compared and aligned for maximum correspondence over a comparison window, or designated region as measured using one of the following sequence comparison algorithms or by manual alignment and visual inspection. Sequences having less than 100% similarity but that have at least one of the specified percentages are said to be "substantially similar." Optionally, this identity exists over a region that is at least about 50 amino acids in length, or more preferably over a region that is at least about 100 to 500 or 1000 or more amino acids in length, or over the full-length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window", and variants thereof, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can also be conducted by the local homology algorithm of Smith and Waterman Add. APL. Math. 2:482 (1981), by the homology alignment algorithm of Needle man and Wunsch J. Mol. Biol. 48:443 (1970), by the search for similarity method of Pearson and Lipman Proc. Natl. Acad. Sci. (U.S.A.) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), Karlin and Altschul Proc. Natl. Acad. Sci. (U.S.A.) 87:2264-2268 (1990), or by manual alignment and visual inspection (see, e.g., Ausubel et al., Current Protocols in Molecular Biology (1995 supplement)).

Examples of an algorithm that is suitable for determining percent sequence identity and sequence similarity include the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information (on the internet at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Standard BLAST algorithm parameters have an expected threshold of 10 (according to the stochastic model of Karlin and Altschul (PNAS, 87:2264-2268 (1990)); a word size of 28; reward and penalty of 1/−2 (a ratio of 0.5, or 1/−2, is used for sequences that are 95% conserved); and a linear GAP cost.

The term "effective amount" refers to an amount (here of COMP-growth factor complexes or aggregates) which provides either subjective relief of a symptom(s) or an objectively identifiable improvement as noted by the clinician or other qualified observer. Determination of an effective amount is well within the capability of those skilled in the art, especially in light of the detailed disclosure provided herein. Generally, an efficacious or effective amount of a combination of one or more polypeptides of the present invention is determined by first administering a low dose or small amount of a polypeptide or composition and then incrementally increasing the administered dose or dosages, adding a second or third medication as needed, until a desired effect of is observed in the treated subject with minimal or no toxic side effects. Applicable methods for determining an appropriate dose and dosing schedule for administration of a combination of the present invention are described, for example, in *Goodman and Gilman's The Pharmacological Basis of Therapeutics,* 11th Edition, 2006, supra; in a Physicians' Desk Reference (PDR), 64$^{th}$ Edition, 2010; in *Remington: The Science and Practice of Pharmacy,* 21$^{st}$ Ed., 2006, supra; and in *Martindale: The Complete Drug Reference,* Sweetman, 2005, London: Pharmaceutical Press., and in Martindale, *Martindale: The Extra Pharmacopoeia,* 31st Edition., 1996, Amer Pharmaceutical Assn, each of which are hereby incorporated herein by reference.

The terms "systemic administration" and "systemically administered" refer to a method of administering the COMP-growth factor complexes or aggregates to a mammal so that the polypeptide or polypeptide composition is delivered to sites in the body, including the targeted site of pharmaceutical action, via the circulatory system. Systemic administration includes, but is not limited to, oral, intranasal, rectal and parenteral (i.e., other than through the alimentary tract, including intramuscular, intravenous, intra-arterial, transdermal and subcutaneous) administration.

The terms "treating" and "treatment" and variants thereof refer to promoting healing, delaying the onset of, retarding or reversing the progress of, alleviating or preventing either the disease or condition to which the term applies, or one or more symptoms of such disease or condition. Treating and treatment encompass both therapeutic and prophylactic treatment regimens.

The terms "subject," "patient," or "individual" interchangeably refer to any mammal, for example, humans and non-human primates, domestic mammals (e.g., canine, feline), agricultural mammals (e.g., bovine, equine, ovine, porcine) and laboratory mammals (e.g., mouse, rat, rabbit, hamster).

The term "isolated," and variants thereof when applied to a protein (e.g., COMP-growth factor complexes or aggregates), denotes that the protein is essentially free of other cellular or tissue components with which it is associated in the natural state. Particularly, it means that the nucleic acid or protein is at least 80%, 85% or 90% free, more preferably at least 95% free, and most preferably at least 99% free of other cellular or tissue components with which it is associated in the natural state.

The term "purified" denotes that a protein or protein complex (e.g., a COMP-growth factor complexes or aggregates) is substantially separated from contaminating components that are not the protein or protein complex. Particularly, it means that the nucleic acid or protein is at least 80%, 85% or 90% pure, more preferably at least 95% pure, and most preferably at least 99% pure.

The terms "targeting moiety," "ligand" or "binding moiety", refer interchangeably to a molecule that binds to a particular target molecule and forms a bound complex as described above. The binding can be highly specific binding, however, in certain embodiments, the binding of an individual ligand to the target molecule can be with relatively low affinity and/or specificity. The ligand and its corresponding target molecule form a specific binding pair. Examples include, but are not limited to small organic molecules, sugars, lectins, nucleic acids, proteins, antibodies and fragments thereof, cytokines, receptor proteins, growth factors, nucleic acid binding proteins and the like which specifically bind desired target molecules, target collections of molecules, target receptors, target cells, and the like.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_{H1}$ by a disulfide bond. The F(ab)'$_2$ may be reduced under mild conditions to break the disulfide linkage in the hinge region thereby converting the (Fab')$_2$ dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker. Huston, et al. (1988) Proc. Nat. Acad. Sci. USA, 85: 5879-5883. While the $V_H$ and $V_L$ are connected to each as a single polypeptide chain, the $V_H$ and $V_L$ domains associate non-covalently. The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to, e.g., g3p (see, e.g., U.S. Pat. No. 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778). Particularly preferred antibodies should include all that have been displayed on phage (e.g., scFv, Fv, Fab and disulfide linked Fv (Reiter et al. (1995) Protein Eng. 8: 1323-1331). Antibody fragments that find use as targeting moieties include without limitation Fab', F(ab')$_2$, Fab, Fab$_2$, H+L (heavy chain+light chain), single domain antibodies, bivalent minibodies, scFv, bis-scFv, tascFv, bispecific Fab$_2$. See, Nelson, et al., *Nature Biotechnology* (2009) 27(4):331-337 and Holliger, et al., *Nature Biotechnology* (2005) 23(9):1126-1136.

The term "specifically binds", as used herein, when referring to a targeting moiety or to a biomolecule (e.g., protein, nucleic acid, antibody, etc.), refers to a binding reaction that is determinative of the presence of the target molecule of the targeting moiety or biomolecule in a heterogeneous population of molecules (e.g., proteins and other biologics). Thus, under designated conditions (e.g., binding assay conditions in the case of a targeting moiety), the specified ligand or targeting moiety preferentially binds to its particular "target" molecule and preferentially does not bind in a significant amount to other molecules present in the sample.

BRIEF DESCRIPTION OF THE DRAWINGS

FIG. 3 A-D illustrate that cofactors affect COMP binding to TGF-β1. A) A pH of 6.75 is optimal for COMP binding to coated TGF-β1. B) The binding of COMP to TGF-β1 is not affected by hydrophobic compounds that bind the pentamerizing domain. C) Increasing concentrations of manganese enhances the binding of COMP to TGF, while similar concentrations of Ca, Mg, and EDTA do not affect the interaction. D) Dose-dependent increase in the amount of COMP bound to TGF in the presence of Mn.

FIG. 4 A-B illustrate electron micrographs of TGF-β1 bound to COMP. A) TGF-β1 binds only to the C-Terminal Domain of COMP in the absence of manganese. B) An additional TGF-β1 binding site is observed in the presence of 10 mM manganese. Schematic shows that each COMP chain can bind a single molecule of TGF-β1 at either site, or both sites can be occupied.

FIG. 5 A-C illustrate binding of COMP(ΔN) to TGF-β1. A) Diagram of N-terminally truncated COMP construct, consisting of the secretion-signal peptide linked to the COMP TSP repeats and C-terminal domain. The pentamerizing domain and EGF-like repeats are missing. B) Soluble TGF-β1 binds to immobilized COMP(ΔN) by ELISA assay in a dose-dependent manner. C) Soluble COMP(ΔN) binds to immobilized TGF-β1 by ELISA in a dose-dependent manner in the presence of manganese. In the absence of manganese, no binding was observed in the range of concentrations used.

FIG. 6 A-B illustrate electron micrographs of TGF-β1 bound to monomeric COMP(ΔN). A) TGF-β1 binds only to the C-Terminal Domain of COMP(LN) in the absence of manganese. B) An additional TGF-β1 binding site is observed within the TSP3 repeats in the presence of 10 mM manganese. Schematic shows that each COMP(ΔN) protein can bind to a single molecule of TGF-β1 at either the site, or both sites can be occupied.

FIG. 10 A-D. A) Schematic representation of truncated COMP monomers: FL:Full-length COMP, T1-T4: truncations involving successive deletions in the TSP Type 3 domain, ΔN: truncation with TSP Type 3- and C-terminal domains. Solid phase ELISAs: (B,C) Binding of COMP and its truncations to TGFβ1 in the absence of $MnCl_2$, differential binding is observed between the different truncations, (D) Binding of COMP and truncations in the presence of $MnCl_2$.

DETAILED DESCRIPTION

1. Introduction

Cartilage oligomeric matrix protein (COMP) is an important non-collagenous cartilage protein that is essential for the structural integrity of the cartilage extracellular matrix. The repeated modular structure of COMP allows it to 'bridge' and assemble multiple cartilage extracellular matrix components such as collagens, matrilins, and proteoglycans. With its modular structure COMP also has the potential to act as a scaffold for growth factors, thereby affecting how and when the growth factors are presented to cell surface receptors. However, it is not known whether COMP binds growth factors. We studied the binding interaction between COMP and chondrogenic and osteogenic growth factors (e.g., TGF-β1 and bone morphogenetic proteins) in-vitro, and determined the effect of COMP on TGFβ1-induced signal transduction in reporter cell lines and primary cells. Our results demonstrate that mature COMP protein binds to multiple TGF-β1 molecules, and that the peak binding occurs at slightly acidic pH. These interactions were confirmed with dual polarization interferometry, and visualized with rotaryshadow electron microscopy. There is cation-independent binding of TGF-β1 to the C-terminal domain of COMP. In the presence of manganese, an additional TGF-β-binding site is present in the TSP-3 repeats of COMP. Data herein further show that COMP-bound TGF-β1 causes increased TGF-β1-dependent transcription. We conclude that TGF-β1 binds to COMP, and that TGF-β1 bound to COMP has enhanced bioactivity.

Figure 1:
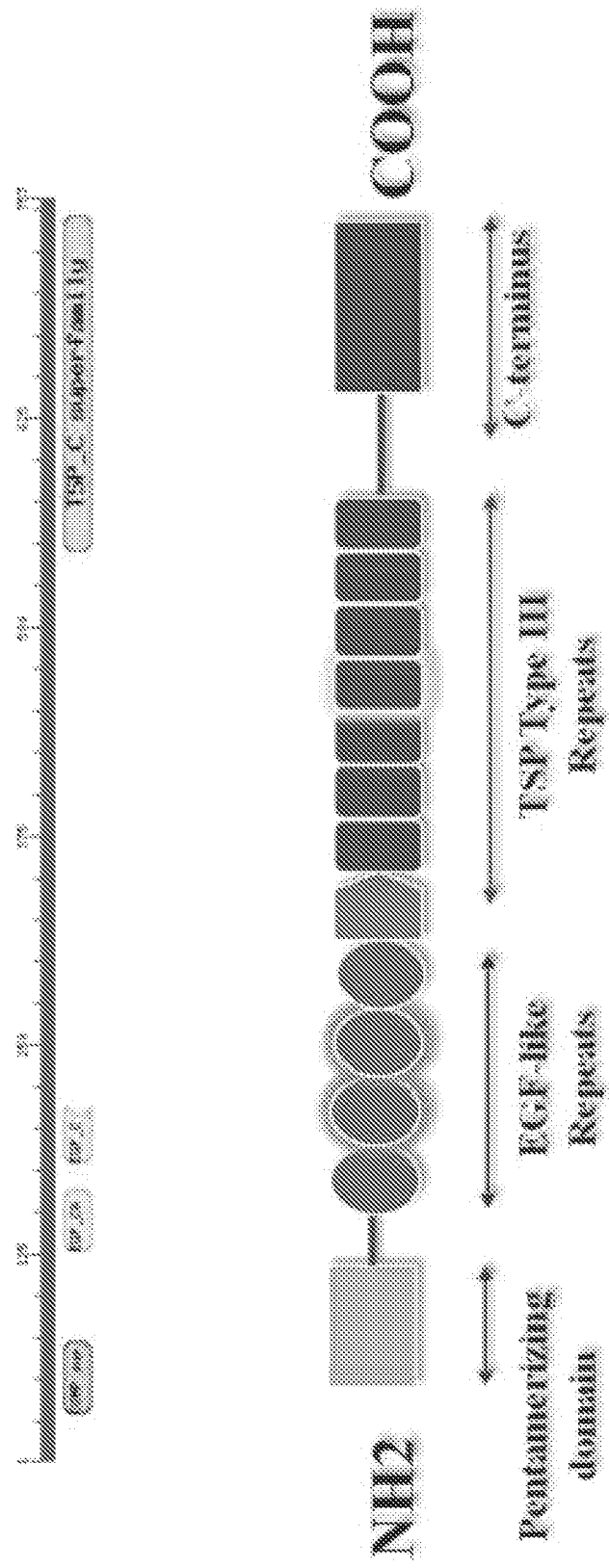
FIG. 1 illustrates conserved domains in a COMP monomer polypeptide sequence. Amino Acids 1-267 include the signal peptide, pentamerizing (N-terminal oligomerizing) domain, and 4 EGF-like domains. Amino acids 268-528 include the TSP3 domains (eight repeats, where the fifth repeat contains an RGD motif; 10 according to Pfam analysis). Amino acids 529 to 757 are the COMP "C-terminal" domain. Amino acid positions are with reference to SEQ ID NO:1.

The present invention is based, in part, on the discovery that each COMP monomer binds multiple growth factor (e.g., TGF-β1 and bone morphogenetic proteins, including BMP2, BMP4, BMP7) molecules, such that COMP increases the local concentration of the growth factor (e.g., FIG. 1). The presentation of multiple growth factor molecules on a COMP scaffold is a more potent and biologically relevant chondrogenic and/or osteogenic stimulus than unbound growth factor (e.g., TGF-β1, and bone morphogenetic proteins, including BMP2, BMP4, BMP7). The present COMP-growth-factor complexes improve capacity for cartilage and/or bone tissue engineering applications and local delivery of growth factor (e.g., TGF-β1 and bone morphogenetic proteins, including BMP2, BMP4, BMP7), to replace or repair injured tissue, e.g., due to traumatic injury or disease.

COMP-growth-factor complexes concentrate growth factor at the site of a cartilage lesion or bone lesion and effectively allow for controlled release of the growth factor at the site to be treated, thus avoiding the need for systemic and bolus administration of the growth factor, and the attendant undesirable side effects. When the growth factor is pre-complexed to a COMP scaffold, it is much more active than the equivalent dose of free soluble growth factor. The COMP-growth factor complexes allow for a reduction in the dose of growth factor, while eliciting a healing response of equivalent or superior efficacy. The COMP-growth factor complexes find use in any situation where it would be beneficial to reduce the total burden of therapeutic unbound growth factor, and the associated undesirable side effects of systemically administered growth factor, without reducing the desired local effect.

2. COMP-Growth Factor Complexes/Scaffolds

The COMP-growth factor protein complexes (also called protein aggregates or protein scaffolds) comprise at least one COMP monomer and at least one growth factor.

In various embodiments, the protein complexes/scaffolds comprise at least 2, 3, 4, 5 or more monomers. The monomers can be arranged in a naturally occurring configuration (e.g., attached via formation of a five-stranded coiled coil and disulfides) or can be attached to a scaffolding (e.g., to a matrix, a solid support). In one embodiment, the COMP-growth factor protein complex/scaffold comprises a COMP pentamer, comprised of five COMP monomers. In various embodiments, the COMP-growth factor protein complex/scaffold can be bound to multiple protein molecules of the same growth factor, or multiple protein molecules of different growth factors. In various embodiments, the stoichiometric ratios of bound growth factor polypeptides to COMP monomers is in the range of about 1:1, 1.2:1, 1.5:1, 1.8:1, 2.1, 2.5:1 or 3:1. In various embodiments, the stoichiometric ratios of bound growth factor polypeptides to a COMP pentamer is in the range of about 5:1, 6:1, 7:1, 8:1, 9:1, 10:1, 11:1, 12:1, 13:1, 14:1 or 15:1.

As appropriate, the COMP-growth factor complexes/scaffolds can be attached to a targeting moiety, e.g., that directs the COMP-growth factor complex/scaffold to a target cell. The target moiety can be any binding moiety that specifically binds to a target of interest, for example, an antibody, antibody fragment or other antigen binding moiety.

a. Cartilage Oligomeric Matrix Protein (COMP) Component

The one or more COMP monomers in a COMP-growth factor protein complex/scaffold can be the same or different. The monomers can be identical or variants of one another. One or more of the monomers can be full-length or truncated.

Table 1 summarizes predicted domains, repeats, motifs and features within a COMP monomer polypeptide, the positions identified with reference to SEQ ID NO:1:

TABLE 1

| Name | Begin | End | E-value |
|---|---|---|---|
| signal peptide | 1 | 22 | — |
| coiled coil | 32 | 65 | — |
| EGF | 90 | 126 | 8.19e−02 |
| EGF_CA | 127 | 179 | 1.67e−07 |
| EGF_CA | 180 | 222 | 1.22e−09 |
| EGF | 228 | 267 | 1.51e+00 |
| Pfam:TSP_3 | 301 | 313 | 1.50e−01 |
| Pfam:TSP_3 | 314 | 329 | 3.50e+00 |
| Pfam:TSP_3 | 337 | 349 | 1.40e+00 |
| Pfam:TSP_3 | 360 | 372 | 5.10e−01 |
| Pfam:TSP_3 | 396 | 408 | 1.10e−01 |
| Pfam:TSP_3 | 419 | 431 | 6.90e−01 |
| Pfam:TSP_3 | 434 | 449 | 2.00e+00 |
| Pfam:TSP_3 | 457 | 469 | 3.50e−01 |
| Pfam:TSP_3 | 493 | 505 | 3.20e−01 |
| Pfam:TSP_3 | 506 | 521 | 2.70e+01 |
| Pfam:TSP_C | 546 | 746 | 2.10e−168 |

The COMP monomers independently can be native polypeptides or variants of the native polypeptides. For example, COMP monomers can be full-length polypeptides or truncated versions or fragments of the full-length polypeptides. For example, the length of the COMP monomer can be 95%, 90%, 85%, 80%, 75%, 70%, 65%, 60%, 55%, 50%, or shorter, of the full-length of the native polypeptide, preferably retaining one or more growth factor binding domains. In some embodiments the truncated COMP monomer retains the TSP_C[pfam05735] domain, located at residues 546-746 of a COMP monomer. In some embodiments the truncated COMP monomer retains the C-terminal COMP domain, e.g., residues 529-757 or residues 527-757. In some embodiments the truncated COMP monomer retains the C-terminal COMP domain, e.g., residues 529-757 or residues 527-757, and one or more EGF-like domains, e.g., within residues 127-216. In some embodiments the truncated COMP monomer retains the C-terminal COMP domain, e.g., residues 529-757 or residues 527-757, the TSP-3 domains, e.g., within residues 268-528, and one or more EGF-like domains, e.g., within residues 127-216. In various embodiments, either one or both of the N-terminal oligomerization domain and/or the EGF-like domains are deleted. The N-terminal oligomerization domain (i.e., COMP [pfam11598]) is located at residues 29-73 of a COMP monomer polypeptide. Calcium-binding EGF-like domains (e.g., pfam07645, smart00179, cd00054) are located approximately at residues 127-(162-163) and at residues 180-(213-216) of a COMP monomer polypeptide. In various embodiments, the signal peptide is retained or deleted, as desired or appropriate. The residue positions are made with reference to SEQ ID NO:1.

Furthermore, a collagen binding domain has been located to amino acid positions 579-595 (Spitznagel, et al., *Biochem J.* (2004) 377(Pt 2):479-87). Accordingly, in some embodiments, the truncated COMP monomer polypeptides can comprise at a minimum amino acid residues 546-746, optionally may comprise residues 527-757, optionally may comprise residues 529-757, and further optionally may comprise amino acid residues within positions 217-757, and further optionally may comprise amino acid residues within positions 127-757. In various embodiments, the truncated COMP monomers have residues 1-73 deleted (retaining residues 74-757), optionally residues 1-126 deleted (retaining residues 127-757), optionally residues 1-163 deleted (retaining residues 164-757), optionally residues 1-126 and 217-528 deleted (retaining residues 127-216 and 529-757), optionally residues 1-267 deleted (retaining residues 268-757), optionally residues 1-526 deleted (retaining residues 527-757), or optionally residues 1-528 deleted (retaining residues 529-757). In some embodiments, the COMP monomer comprises an N-terminal oligomerization domain (i.e., COMP [pfam11598]) and a TSP_C [pfam05735] domain. The residue positions are made with reference to SEQ ID NO:1.

In various embodiments, the COMP monomer comprises an N-terminal oligomerization domain, at least eight (8) contiguous TSP-type 3 domains and a C-terminal COMP domain (e.g., truncated COMP polypeptide T1 depicted in FIG. 10A, e.g., residues 29-73 and 268-757, e.g., residues 32-65 and 301-746, e.g., residues 32-65 and 314-746, e.g., residues 32-65 and 337-746); the EGF-like domains are deleted. In various embodiments, the COMP monomer comprises an N-terminal oligomerization domain, seven (7) contiguous TSP-type 3 domains and a C-terminal COMP domain (e.g., truncated COMP polypeptide T2 depicted in FIG. 10A, e.g., residues 32-65 and 360-746); the EGF-like domains are deleted. In various embodiments, the COMP monomer comprises an N-terminal oligomerization domain, six (6) contiguous TSP-type 3 domains and a C-terminal COMP domain (e.g., truncated COMP polypeptide T3 depicted in FIG. 10A, e.g., residues 32-65 and 396-746); the EGF-like domains are deleted. In various embodiments, the COMP monomer comprises an N-terminal oligomerization domain, five (5) contiguous TSP-type 3 domains and a C-terminal COMP domain (e.g., truncated COMP polypeptide T4 depicted in FIG. 10A, e.g., residues 32-65 and 419-746); the EGF-like domains are deleted. In various embodiments, the COMP monomer comprises at least eight (8) contiguous TSP-type 3 domains and a C-terminal COMP domain (e.g., truncated COMP polypeptide ΔN depicted in FIG. 10A, e.g., residues 268-757, e.g., residues 301-746, e.g., residues 314-746, e.g., residues 337-746); the N-terminal oligomerization domain and the EGF-like domains are deleted. The residue positions are made with reference to SEQ ID NO:1.

Furthermore, analogs including allelic, species and induced variants of COMP monomer polypeptides find use. Analogs or variants of the COMP monomer polypeptides can differ from naturally occurring peptides. In various embodiments, the COMP monomers can differ at up to 30%, e.g., up to 20%, 15%, 10%, or 5% of amino acid positions, or by, e.g., up to 1, 2, 3, 4, 5, 6, 7, 8, 9 or 10 position changes. For example, in some embodiments, an analog may vary by up to 1, 2, 3, 4, 5 or 6 position changes. Each deletion or substitution of a natural amino acid residue is considered a position change as is the insertion of a residue without substitution. Amino acids substitutions are often conservative. For purposes of classifying amino acids substitutions as conservative or non-conservative, amino acids are grouped as follows: Group I (hydrophobic sidechains): norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class. Non-conservative substitutions constitute exchanging a member of one of these classes for a member of another.

In various embodiments, the COMP monomers include polypeptides that are "substantially identical" or exhibit "substantial similarity." For example, the COMP monomer polypeptides can have at least 60% identity, optionally at least 65%, 70%, 75%, 80%, 85%, 90%, 95%, 98%, or 99% amino acid sequence identity to the native polypeptides (e.g., SEQ ID NO:1), or truncated sequences thereof, as described herein, when compared to the native polypeptides and aligned using sequence comparison algorithms or by manual alignment and visual inspection using methods known to those of skill in the art. In some embodiments, the COMP monomers are identical to or have 100% sequence identity to SEQ ID NO:1, or truncated sequences thereof.

In various embodiments, one or more COMP monomer amino acid residues Thr527, Leu528, Thr529, Asn555, Arg558, Asp581, Glu583, Arg683, Trp684, Phe685, Gln687, Tyr694, Arg696, Arg698, Tyr700, Pro703, Glu704, Leu705, Asp708, Asn710, Val711, Asn736, Arg738, Arg740, Cys741, Asn742, Pro746, Glu747, Asp748, Thr751, or Arg755 are substituted (e.g., conservatively or non-conservatively), or deleted.

In various embodiments, the COMP monomers can be fused with a second polypeptide. For example, a COMP monomer can be fused to additional growth factor binding domains. In some embodiments, the COMP monomer is fused to one or more TSP_C[pfam05735] domains, e.g., one or more amino acid peptide sequences comprising residues 546-746 of SEQ ID NO:1. The additional growth factor binding domains can be in tandem, expressed as contiguous sequence segments, or spaced with linker sequences inbetween. In other embodiments, the COMP monomer is fused to a heterologous second polypeptide (e.g., a polypeptide that is not COMP). For example, the second polypeptide can be a targeting moiety, for example, an antibody or antibody fragment. In some embodiments, the growth factor binding domain of a COMP monomer is fused to the oligomerization domain of a heterologous polypeptide.

b. Growth Factor Component

The COMP-growth factor complexes are bound to one or more growth factor polypeptides, preferably multiple growth factor polypeptides. The one or more growth factors can be the same or different. The COMP-growth factor complexes can be bound to a single growth factor species, or alternatively, to 2, 3, 4, 5 or more different growth factors, effectively providing a scaffold for a growth factor cocktail. Any growth factors that bind to a COMP monomer find use. Growth factors that bind to the TSP_C [pfam05735] domain find particular use.

In some embodiments, the one or more growth factors are a member of the transforming growth factor-beta 1 (TGF-β1) superfamily. "TGF-β superfamily protein" can be any protein of the art-recognized superfamily of extracellular signal transduction proteins that are structurally related to TGF-β1-5. A TGF-β superfamily protein suitable for use in the present COMP complexes, includes without limitation TGF-β1, TGF-β2, TGF-β3, TGF-β4, TGF-β5, bone morphogenetic protein (BMP)-2, BMP-3, BMP-4, BMP-5, BMP-6, BMP-7, BMP-8, BMP-9, cartilage-derived morphogenetic protein (CDMP)-1, CDMP-2, and/or CDMP-3. More preferably, the chondrogenesis- and/or osteogenesis-enhancing proteins useful in the composition of the present invention include, but are not limited to: TGF-β1, TGF-β2, TGF-β3, BMP-2, BMP-3, BMP-4, BMP-5, BMP-6, BMP-7, and/or CDMP (CDMP-1, CDMP-2, and/or CDMP-3).

In some embodiments, the one or more growth factors are a bone morphogenetic protein (BMP). In some embodiments, the one or more growth factors are selected from the group consisting of TGF-β1, bone morphogenetic protein (BMP)-2, BMP-3, BMP-4, BMP-5, BMP-6 and BMP-7. In some embodiments, the one or more growth factors are selected from the group consisting of TGF-β1, BMP-2, BMP-3, BMP-4, BMP-5, BMP-6, BMP-7, fibroblast growth factor-2 (FGF-2), hepatic growth factor (HGF), vascular endothelial growth factor (VEGF) and insulin-like growth factor 1 (IGF-1). In some embodiments, the one or more growth factors are selected from the group consisting of fibroblast growth factor-2 (FGF-2), hepatic growth factor (HGF), vascular endothelial growth factor (VEGF) and insulin-like growth factor 1 (IGF-1).

3. Matrices Comprising COMP-Growth Factor Complexes/Scaffolds

The COMP-growth factor complexes/scaffolds can be contained within a matrix. The matrix can serve, in one capacity, as a delivery vehicle for the composition to be delivered to the site of a cartilage lesion or a bone lesion. The matrix also provides a suitable scaffold upon which cartilage repair and regeneration can occur. In one embodiment, the matrix is bioresorbable or biodegradable.

In various embodiments, the matrix can be formed of any material that is suitable for in vivo use, and which provides the characteristics facilitating cartilage repair or bone repair in conjunction with the COMP-growth factor complexes/scaffolds. The matrix can be formed of materials which include, but are not limited to, synthetic polymers and/or a ground substance. Preferred ground substances include natural polymers and proteoglycans. Natural polymers include, but are not limited to collagen, elastin, reticulin and analogs thereof. Proteoglycans include, but are not limited to, any glycosaminoglycan-containing molecules. Particularly preferred glycosaminoglycans include chondroitin sulfate, dermatan sulphate, heparan sulphate, keratan sulphate and hyaluronan. Other preferred ground substances include, but are not limited to, type I collagen, type II collagen, type III collagen, type IV collagen and hyaluronic acid. Preferred synthetic polymers include poly(lactic acid) and poly(glycolic acid).

In one embodiment of the present invention, the matrix includes collagen. For example, the matrix can contain from about 20% to about 100% collagen by dry weight of the matrix, for example, from about 50% to about 100% collagen by dry weight of the matrix, for example, from about 75% to about 100% collagen by dry weight of the matrix.

A matrix suitable for use with the COMP-growth factor complexes/scaffolds can include materials in any suitable form for use in repairing a cartilage lesion or a bone lesion, including a sponge, a membrane, a film or a gel. In one embodiment, a suitable repair matrix includes demineralized bone matrix, synthetic bone graft substitute, autograft tissue, allograft tissue and/or xenograft tissue. In some embodiments, the matrix is formulated for use as a bone graft, for example, as a spinal graft.

Suitable methods for associating a COMP-growth factor complex/scaffold with a matrix include any method which allows the proteins to be delivered to a site of cartilage repair or bone repair together with the matrix such that the cartilage repair or bone repair product is effective to repair and/or regenerate cartilage or bone at the site. Such methods of association include, but are not limited to, suspension of the composition within the matrix, freeze-drying of the composition onto a surface of the matrix and suspension within the matrix of a carrier/delivery formulation containing the composition. Additionally, the COMP-growth factor complex/scaffold can be associated with the matrix prior to placement of the product into a cartilage lesion (i.e., the association of the composition with matrix occurs ex vivo) or alternatively, the matrix can first be implanted into a lesion, followed by association of the COMP-growth factor complex/scaffold with the matrix, such as by injection into or on top of the matrix (i.e., the association of the composition with matrix occurs in vivo).

A COMP-growth factor complex/scaffold can contain additional delivery formulations or carriers which enhance the association of the composition with the matrix, which enhance the delivery of the composition to the appropriate cells and tissue at the site of the lesion, and which assist in controlling the release of the factors in the composition at the site of the lesion. Suitable delivery formulations include carriers, which, as used herein, include compounds that increase the half-life of a cartilage-inducing composition in the treated animal. Suitable carriers include, but are not limited to, polymeric controlled release vehicles, biodegradable implants, liposomes, bacteria, viruses, oils, cells, esters, and glycols. Preferably, the matrices are bioresorbable or biodegradable.

In various embodiments the carrier for the COMP-growth factor complex/scaffold is formulated at a pH in the range of about 5.5 to about 7.25, for example, in a pH range of about 5.75 to about 6.75. In embodiments where the COMP-growth factor complex/scaffold is complexed with TGF-β1 as the only growth factor, the carrier can be formulated to have a pH in a range of about 6.75 to about 7.25. In embodiments where the COMP-growth factor complex/scaffold is complexed with BMP polypeptides, e.g., BMP-2, BMP-3, BMP-4, BMP-5, BMP-6, and/or BMP-7, the carrier can be formulated to have a pH in a range of about 5.5 to about 5.75. The carrier may also further include manganese (Mn2+), e.g., at a concentration in the range of about 10-50 mM, e.g., at a concentration of about 10 mM, 15 mM, 20 mM, 25 mM, 30 mM, 35 mM, 40 mM, 45 mM or 50 mM.

COMP-growth factor complexes/scaffolds are present in the matrix at a concentration that is effective to induce, at the site of a cartilage lesion or a bone lesion, one or more of: cellular infiltration, cellular proliferation, angiogenesis, and cellular differentiation to type II collagen-producing chondrocytes. Preferably, the COMP-growth factor complexes/scaffolds are present in the matrices at a concentration that is effective to induce cartilage repair and/or regeneration at the site of a cartilage lesion or a bone lesion. One of skill in the art will be able to adjust the concentration of proteins and/or nucleic acid molecules in the composition depending on the types and number of proteins to be provided by the composition, and the delivery vehicle used.

The matrices can also contain one or more substances that non-covalently attach to the COMP-growth factor complexes/scaffolds in the composition and thus, modify the release rate of the growth factor. Such substances include, but are not limited to, any ground substance or other polymeric substance. As used herein, a ground substance is defined as the non-living matrix of connective tissue, which includes natural polymers and proteoglycans. Natural polymers include, but are not limited to collagen, elastin, reticulin and analogs thereof. Proteoglycans include, but are not limited to any glycosaminoglycan-containing molecules, and include chondroitin sulfate, dermatan sulphate, heparan sulphate, keratan sulphate and hyaluronan. Preferred ground substances include, but are not limited to, type I collagen, type II collagen, type III collagen, type IV collagen and hyaluronic acid. Preferred other polymeric substances include, but are not limited to, poly(lactic acid) and poly(glycolic acid).

In a further embodiment, the matrices can include one or more types of cells which are provided to further enhance chondrogenesis at the site of the cartilage lesion. Such cells include, but are not limited to, fibrochondrocytes, chondrocytes, mesenchymal precursors, and any other cell that can serve as a chondrocyte precursor. Such cells can be associated with the composition and the matrix by any of the methods described above.

In some aspects of the present invention, matrices comprising the COMP-growth factor complexes/scaffolds further comprise at least one bone matrix protein. As used herein, "bone matrix proteins" are any of a group of proteins known in the art to be a component of or associated with the minute collagenous fibers and ground substances which form bone matrix. As used herein, a bone matrix protein is not a member of the TGF-β superfamily as described herein, nor a growth factor protein as described herein. Bone matrix proteins can include, but are not limited to, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and/or fibronectin. Preferably, bone matrix proteins suitable for use with the product of the present invention include one or more of: osteocalcin, osteonectin, MGP, TSP, BSP, lysyloxidase and cathepsin L pre. In one embodiment, the at least one bone matrix protein includes at least osteocalcin, osteonectin, BSP, lysyloxidase and cathepsin L pre. A particularly preferred bone matrix protein is MGP, and more preferred is osteonectin, and most preferred is TSP.

The COMP-growth factor complexes/scaffolds and matrices comprising the complexes/scaffolds are useful for repairing a variety of defects in cartilage, including both tears and segmental defects in both vascular and avascular cartilage tissue. The product is particularly useful for repairing defects in hyaline (e.g., articular) and/or fibrocartilage (e.g., meniscal). For example, the COMP-growth factor complexes/scaffolds find use in repairing a meniscal radial tear; a meniscal triple bucket handle tear; a longitudinal tear in the avascular area of a meniscus; or a meniscal segmental lesion.

Because cartilage defects and bone defects (i.e., lesions) can occur in a variety of shapes, sizes, and locations, a matrix comprising the COMP-growth factor complexes/scaffolds is of a shape and size sufficient to conform to a specific defect in the cartilage or the bone of the patient to be treated. Preferably, the matrix, when used in the repair of a cartilage defect or bone defect, achieves a geometry at the defect site that is suitable to provide a therapeutic benefit to the patient. Such a therapeutic benefit can be any improvement in a patient's health and well-being that is related to a correction of the cartilage defect or the bone defect, and preferably, the therapeutic benefit includes the repair of the defect such that the natural configuration of the cartilage or the bone is at least partially restored. The matrix can be fixed or implanted directly into a cartilage lesion or a bone lesion.

4. Methods of Promoting Chondrogenesis and Bone Repair

With or without a matrix, the COMP-growth factor complexes/scaffolds find use in promoting chondrogenesis. Chondrogenesis is promoted or increased by contacting a cell capable of producing cartilage with a COMP-growth factor complex/scaffold, such that the growth factor is delivered to the cell at a concentration sufficient to induce signaling and the desired effect of cartilage production. The cell capable of producing cartilage may be a chondrocyte or a chondrocyte precursor, or a stem cell (e.g., a mesenchymal stem cell or a bone marrow stem cell). The cell may be in vivo or in vitro. In some embodiments, the COMP-growth factor complexes/scaffolds are administered to a subject and delivered directly to a cartilage lesion to be repaired. In other embodiments, the COMP-growth factor complexes/scaffolds are administered systemically to the subject, e.g., intravenously, subcutaneously, intramuscularly. In various embodiments of methods for promoting chondrogenesis, the COMP-growth factor complex/scaffold comprises one or more TGF-β1 polypeptides.

With or without a matrix, the COMP-growth factor complexes/scaffolds further find use in promoting bone repair and bone healing. Bone repair is promoted or increased by contacting a bone lesion with a COMP-growth factor complex/scaffold, such that the growth factor is delivered to the bone lesion at a concentration sufficient to induce signaling and the desired effect of bone repair and/or bone healing. The cell capable of producing bone may be an osteoblast or an osteoblast precursor, or a stem cell (e.g., a mesenchymal stem cell or a bone marrow stem cell). The cell may be in vivo or in vitro. In some embodiments, the COMP-growth factor complexes/scaffolds are administered to a subject and delivered directly to a bone lesion to be repaired. In other embodiments, the COMP-growth factor complexes/scaffolds are administered systemically to the subject, e.g., intravenously, subcutaneously, intramuscularly. In various embodiments of methods for promoting osteogenesis, the COMP-growth factor complex/scaffold comprises one or more BMP polypeptides.

The COMP-growth factor compositions can be formulated in one or more pharmaceutically acceptable excipients. A suitable pharmaceutically acceptable excipient is capable of maintaining a protein in a form that, upon arrival of the protein at the delivery site, the protein is biologically active such that chondrogenesis or osteogenesis at the site is enhanced. Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity. Particularly preferred excipients include non-ionic diluents, with a preferred non-ionic buffer being 5% dextrose in water (DW5). Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal,—or o-cresol, formalin and benzol alcohol. COMP-growth factor complex/scaffold compositions can be sterilized by conventional methods and/or lyophilized.

The COMP-growth factor complexes/scaffolds find numerous orthopaedic applications for delivering a TGF-β1 superfamily growth factor, e.g., to a bone lesion or a cartilage lesion, including without limitation bone fractures, spinal fusions, osteoarthritic lesions, and tendon and ligament repair:

Fracture non-union and critical size defects, for example, tibial shaft fractures, distal tibial fractures, tibial nonunions, scaphoid nonunion, diaphyseal humeral nonunions long bone nonunions, clavicle nonunions Osteoarthritis (e.g., of the knee, hip, hand, ankle, etc.)

Cartilage and Bone and Osteochondral tissue engineering

Spinal Fusions for Degenerative Disc Disease, back pain
  ALIF surgery (Anterior Lumbar Interbody Fusion)
  PLIF (Posterior Lumbar Interbody Fusion)
  TLIF (Transforaminal Lumbar Interbody Fusion)
  Intradiscal injections
  As an adjunct to iliac crest autograft, or replacement for autograft Bone-inductive coverings of Implants in Dental and Orthopaedic uses Treatments for alveolar bone loss Wedge Osteotomies Treatment for Rotator Cuff Tears Tendon and Ligament repair Additionally, the COMP-growth factor complexes/scaffolds can be used to deliver a growth factor to a target cell. For example, a COMP scaffold bound to one or more TGF-β1 polypeptides can be delivered to a skin lesion to prevent, reduce or reverse scarring.

EXAMPLES

The following examples are offered to illustrate, but not to limit the claimed invention.

Example 1

Enhanced Activity of TGF-β1 Bound to Cartilage Oligomeric Matrix Protein

Experimental Procedures

Recombinant human COMP and TGF-β1—

Human COMP cDNA in the pQE mammalian expression vector (Qiagen) was stably transfected into human 293T cells (ATCC), which were cultured in serum-free media. Recombinant human COMP (rhCOMP) was purified from the cell culture media to near homogeneity by nickel-NTA column affinity chromatograph. An N-terminally truncated COMP construct (COMP-ΔN), having the thrombospondin-3 domains and the C-terminal domain (amino acids 269-757 of human COMP, shown in FIG. 5A) was similarly expressed and purified from 293T cell culture supernatants. The truncated COMP is missing the pentamerizing domain and EGF repeats, and is secreted as a monomeric protein with an apparent molecular weight of approximately 80 kDa. Human TGF-β1 was purchased from PeproTech (Rocky Hill, N.J.), in a carrier-free formulation. Its activity was confirmed in pellet culture chondrogenesis assays of bone marrow-derived human stem cells. Recombinant human BMP-7 was a generous gift from Dr. David Rueger, Stryker Biotech, Hopkinton Mass., to A. Hari Reddi. Human BMP-2 and BMP-4 were purchased from R&D Systems, Minneapolis, Minn.

Solid Phase ELISA Binding Assays—

TGF-β1 was coated onto ELISA plates at 0.5 μg/ml or 1 μg/ml in 50 mM sodium carbonate, pH 9.8. In certain experiments, COMP constructs were similarly coated at 1 μg/ml. Unbound sites were blocked with phosphate buffered saline (PBS) containing 1% heat-denatured BSA and 0.05% Tween-20 at pH 7.30 (PBS-TB). COMP protein was diluted in Tris buffered saline with 1% heat denatured BSA and 0.05% Tween-20 at pH 7.35 (TBS-TB) and allowed to bind overnight. COMP concentrations ranged between 0.06 μg/ml and 20 μg/ml, which corresponds to 140 pM to 46 nM, using a calculated molecular mass of 433 kDa for the COMP pentamer (Zaia, et al., (1997) *J Biol Chem* 272; 14120-14126). For lower pH experiments PIPES buffer was used instead of Tris. When indicated, divalent cations Mg, Ca, and Mn were added as chloride salts throughout all binding, washing, and incubation steps. When indicated, COMP was pre-incubated with 2 μM of retinoic acid or vitamin D, diluted at least 1:5000 from DMSO stock. Bound COMP was detected with polyclonal rabbit anti-COMP generated in-house. TGF-β1 was detected with monoclonal antibody MAB240 (R&D Systems) and BMP-7 with monoclonal antibody MAB3541. In all cases, detection of the primary antibody was performed with a peroxidase-conjugated anti-rabbit secondary antibody. For colorimetric detection, TMB-Turbo substrate (Pierce) was added for 2 minutes, the reaction was stopped with 2M sulfuric acid, and absorbance was measured at 450 nm on a 96-well microplate reader. For COMP binding to immobilized TGFβ1, the background of COMP binding to immobilized BSA was subtracted. Assays were performed in triplicate and reproduced.

Negative Staining Electron Microscopy—

TGF-β1 was labeled for negative staining with colloidal thiocyanate gold and allowed to form complexes with COMP by incubation for 30 minutes at RT in Tris buffered saline (pH 7.4) with 10 mM manganese chloride. Complexes between TGF-β and COMP were analyzed by negative staining and electron microscopy, as described previously (Bengtson, et al., (2008) *J Innate Immun* 1, 18-28). The specimens were finally examined in a JEOL 1200EX transmission electron microscope operated at 60 kV.

Dual Polarization Interferometry—

DPI analysis was performed using an AnaLight4D Workstation (Farfield Group, Manchester UK), with COMP immobilized onto AnaChip Plus His-Tag chips. Soluble TGF-β1 was bound to the immobilized COMP at the indicated concentrations, and nonspecific sites blocked with digested casein. Binding was performed in a buffer containing 25 mM PIPES pH 7.2, 150 mM NaCl, and no manganese. Data collection and analysis were performed using the AnaLight Software Suite and AnaLight Explorer, respectively. The DPI instrument provides absolute measurements of the change in the thickness and density of the molecular protein layer, which enables a calculation of the mass of the immobilized COMP as TGF-β was added. These measurements are directly related to the structure and function of COMP and its interactions with TGF-β in close proximity to the measurement surface and provide the ability to determine binding constants and stoichiometry of binding.

Luciferase Assays for Transcriptional Activation—

To test the effect of COMP on TGF-β-dependent transcriptional activation, we assayed the activation of a TGF-β-responsive promoter that had been stably transfected into a mink lung epithelial cell line (PAI-1/luciferase cells kindly provided by Dr. Rifkin at NYU) (Abe, et al., (1994) *Anal Biochem* 216, 276-284). First we determined that the mid-range of the TGF-β-response was 4.6 ng/ml using our batch of TGF-β1 (data not shown). Next, a constant amount of TGF-β1 (4.6 ng/ml) was mixed with increasing concentrations of COMP in a chemically defined low-protein medium (Opti-MEM supplemented with 50 μM manganese chloride). After 30 hours, luciferase activity was assayed in the cell lysate using the Dual Luciferase Assay Reporter System (Promega) with readings normalized to cell seeding density.

Quantitative RT-PCR—

Three strains of human bone marrow stem cells (BMSCs) were obtained from different donors, and maintained as stem cells in alpha-MEM supplemented with 10% fetal bovine serum (FBS) and 5 ng/ml FGF2. Cells at passage 2 were transduced with lentiviral constructs to express either full length human COMP or green fluorescent protein (GFP), and untransduced BMSCs were used as control. COMP overexpression was confirmed by Western blotting of 20 µl cell culture supernatant with anti-COMP antibody. Cells were seeded in 6-well dishes at $2\times10^4$ cells/well, allowed to attach in alpha-MEM with 10% FBS, and then treated with TGF-β1 for 48 hours. Total RNA was isolated (RNeasy Micro reagents, Qiagen, Valencia Calif.). The mRNA expression of the TGF-β-response gene thrombospondin-1 (TSP1) was quantified with TaqMan probe Hs00962908_m1 (Applied Biosystems) and TaqMan Fast Universal PCR reagents with a 7900HT-Fast thermocycler (Applied Biosystems). Relative expression of TSP1 was normalized to the level of 18S RNA in each sample, and fold-change in TSP1 expression between samples was calculated using the 2ΔΔCt method.

Docking Simulation—

Docking simulation was performed as described previously (Saegusa, et al., (2008) *J Biol Chem* 283, 26107-26115; Mori, et al., (2008) *J Biol Chem* 283, 18066-18075) using AutoDock3 (Morris, et al., (1998) *Journal of Computational Chemistry* 19, 1639-1662) and ADT (Sanner, M. F. (1999) *J Mol Graph Model* 17, 57-61). We performed 50 dockings of the TGF-β1-COMP interaction, each one starting with a random initial position and orientation of TGF-β1 (PDB code 3KFD, fragment A) with respect to the COMP C-terminal domain (amino acids 527 to 757, PDB code 3FBY, fragment A).

Statistical Analysis—

Experimental analysis was performed in triplicate, with key experiments repeated at least three times. Error bars represent standard deviations. Unless otherwise noted, statistical comparisons were made using JMP software (SAS, Cary N.C.) and 2-sided t-tests with significance set at $p<0.05$.

Results

Binding of COMP to TGF-β and BMP Ligands.

Figure 2E:
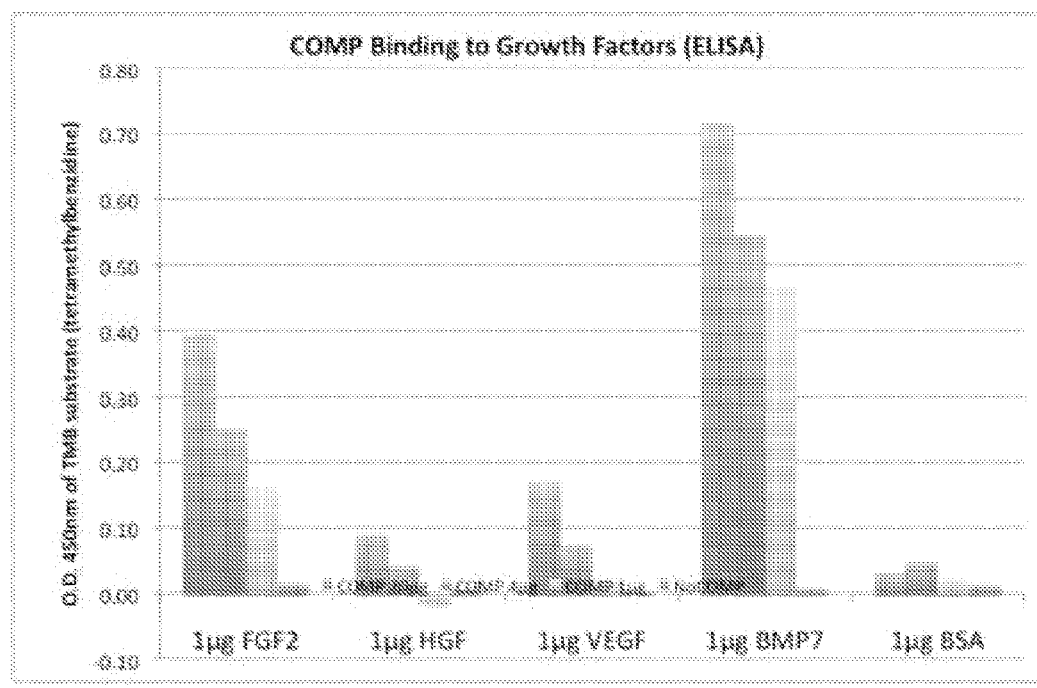
FIG. 2 A-E illustrate binding of COMP to TGF-β and BMP by ELISA. A) Soluble COMP binds to all TGF-β superfamily proteins tested, namely TGF-β1, BMP-2, -4, and -7. B-C) Soluble TGF-β1 and BMP-7 bind to immobilized COMP in a dose-dependent manner. D) Soluble COMP binds to immobilized TGFβ1 in a dose-dependent and saturable manner. For all assays, COMP, TGF-β1 and BMP-7 were coated at 1 μg/ml, BMP-2 and -4 were coated at 0.5 μg/ml. Blocking was with 1% denatured BSA, and binding conditions were performed in 150 mM NaCl with 16 mM calcium chloride, 0.05% Tween-20, and 50 mM Tris pH 7.35, and background binding to BSA-coated wells was subtracted. E) COMP binds to various growth factors including FGF2, HGF, VEGF, and BMP7.

The TGF-β superfamily of proteins in humans includes three TGF-β isoforms and the bone morphogenetic proteins (BMPs). To determine whether COMP binds to members of the TGF-β family of ligands, we performed solid-phase binding assays using soluble COMP and immobilized TGFβ1, BMP-2, -4, and -7. We found that soluble COMP bound to immobilized TGF-β1, BMP-2, BMP-4, and BMP-7 (FIG. 2A). To confirm the specificity of the binding interactions, we repeated these assays with immobilized COMP and soluble TGF-β1 and BMP-7 (FIGS. 2B and 2C). We found that the binding interactions were reproducible when performed with either COMP or BMP-7/TGF-β in the soluble phase. These results demonstrate that COMP binds to TGF-β1, BMP-2, BMP-4, and BMP-7. In fact, COMP bound to every member of the TGF-β superfamily we tested.

Soluble COMP bound to immobilized TGF-β1 in a dose-dependent and saturable manner in the presence of calcium chloride (FIG. 2D). This was reproducible in the absence of calcium chloride. Analysis of the binding curve indicates that half-maximal binding occurs at approximately 1.4 µg COMP binding to 1 µg TGF-β1, which very roughly corresponds to 14 molecules of TGF-β1 bound to each pentameric COMP protein, and suggests that multiple TGF-β1 molecules interact with a single molecule of COMP.

pH Preference of COMP-TGF-β1 Binding.

We next determined the pH preference at which COMP binds to TGF-β1. Solid-phase ELISA assays were performed as described above, but at varying pH. When the pH of the binding buffers was adjusted between 6.5 and 7.5 in 0.25 increments, the maximal amount of TGF-β1 binding was found at pH 6.75 (FIG. 3A). The binding dropped off rapidly at pH 7.25 and higher.

Effect of Cofactors on the COMP-TGF-β1 Interaction.

The hydrophobic core formed by the COMP pentamerizing domains binds to hydrophobic molecules such as retinol and vitamin D. We used solid phase binding assays to test whether the presence of these hydrophobic molecules affects COMP binding to TGF-β. We did not observe any change in the COMP-TGF-β1 interaction, even in the presence of relatively high concentrations of retinol and vitamin D used in the assays (FIG. 3B).

In addition to binding hydrophobic compounds in its pentamerizing domain, there are up to 30 cation-binding sites in COMP, many of which are occupied by calcium ions (Tan, et al., (2009) *FASEB J* 23, 2490-2501). We therefore tested whether different cations or EDTA would affect the binding interaction between soluble COMP and immobilized TGF-β1 using ELISA assays. A constant amount of COMP was allowed to bind the immobilized TGF-β1 in the presence of increasing concentrations of calcium or other divalent cations (Ca, Mg, Mn, or EDTA). We found that manganese caused a dose-dependent increase in the amount of COMP bound to TGF-β1 (FIG. 3C). However, the binding of COMP to TGF-β1 was not affected by the addition of either calcium or magnesium to 40 mM. Surprisingly, EDTA up to 40 mM also did not affect the binding interaction (FIG. 3C). To further characterize the effect of manganese on the TGF-β-COMP interaction, increasing amounts of soluble COMP were bound to immobilized TGF-β1 in the presence or absence of 10 mM manganese. We observed a shift in the binding curve, indicating that higher affinity binding interactions occur in the presence of manganese (FIG. 3D).

Additional TGF-β1 Binding Sites with Manganese.

The observation that manganese increased the base-line binding of COMP to TGF-β1 raised the question whether the presence of manganese unmasks additional binding sites for TGF-β in each COMP monomer. Alternatively, manganese could simply enhance the affinity of a single TGFβ-binding site. To discern between these possibilities, we obtained negative stained electron micrographs of gold-labeled TGF-β1 bound to COMP in the presence and absence of manganese. In the absence of manganese, TGF-β1 bound only to the CTD globule of COMP (FIG. 4A). In the presence of 10 mM manganese, TGF-β1 bound to an additional site closer to the N-terminus of COMP (FIG. 4B). In the presence of manganese, TGF-β1 occupied either the N-terminal site, or the CTD binding site, or both sites on a single arm of the pentameric COMP protein. We also observed that TGF-β simultaneously bound to multiple arms of a single COMP pentamer. These results support the hypothesis that two TGF-β-binding sites exist on each COMP polypeptide, and that manganese is a required co-factor for one of these sites.

Manganese-dependent TGF-β binding of COMP-ΔN.

From the electron micrographs, the manganese-dependent TGF-β1 binding site could be located within either the EGF-like domains or the TSP3 repeats of COMP. To address this question, we generated and purified an N-terminally truncated COMP protein (COMP-ΔN), in which the secretion signal peptide was fused to C-terminal amino acids 269-757. The COMP-ΔN construct contains all TSP-3 repeats and the COMP CTD, but it is missing the pentamerizing domain and the 4 EGF domains (FIG. 5A). We found that soluble TGF-β1 bound to immobilized COMP-ΔN in a dose-dependent manner, as measured by ELISA in the absence of manganese (FIG. 5B). Similarly, soluble COMP-ΔN bound to immobilized TGF-β1 in a dose-dependent manner (FIG. 5C). We tested whether the binding of COMP-ΔN to immobilized TGF-β1 was dependent on the presence of manganese. While strong binding was observed in the presence of manganese, we did not detect binding in its absence in this particular assay.

Electron micrographs of TGF-β1 interacting with COMP-ΔN paralleled the observations made with full length COMP. TGF-β1 bound to the CTD in a manganese independent manner (FIG. 6A), whereas binding to the more N-terminal region was only observed in the presence of manganese (FIG. 6B). Based on these electron micrographs, the manganese-dependent binding site is located within the TSP3 repeats of COMP. Taken together, these observations confirm that the CTD of COMP contains a manganese-independent TGF-β-binding site, and that an additional manganese-dependent site is located within the TSP3 repeats. TGF-β1 bound to either the CTD, or the TSP3 repeats, or both sites on a single COMP-ΔN peptide.

Quantitative Measurement of Stoichiometry.

Figure 7:
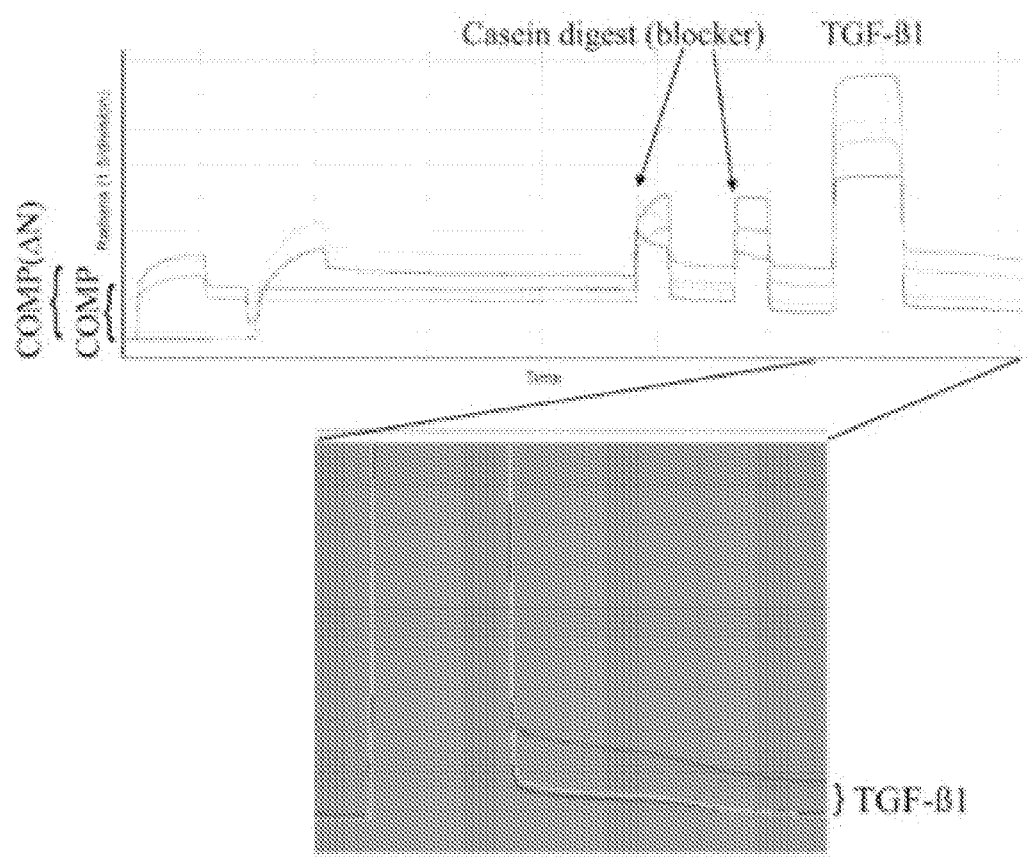
FIG. 7 illustrates binding Affinity and Stoichiometry of the COMP-TGF-β Interaction by DPI analysis. Analysis indicates that full length COMP(FL) binds approximately 11.5 TGF-β1 molecules. The apparent dissociation constant in the nM range is consistent in both full length and truncated COMP. COMP(FL) and COMP(ΔN) were coated onto a HisTag AnaChip-Plus chip in an AnaLight4D DPI instrument. The binding of soluble TGF-β1 was performed at pH 7.35 without manganese.

A more quantitative analysis of binding stoichiometry was obtained using dual polarization interferometry (DPI) performed on an AnaLight4D DPI instrument (Farfield Group). This instrument provides a quantitative measurement of the change in the mass of immobilized COMP protein as TGFβ1 is added in solution. The number of TGF-β1 molecules bound to each COMP molecule, as well as a binding affinity of the interaction, can be calculated from this data. A binding stoichiometry of 11.5 molecules TGF-β1 per COMP pentamer was determined, with the dissociation constant for the interaction roughly estimated to be in the nM range (FIG. 7). This stoichiometry measurement is in agreement with the ELISA estimate presented above. Using the same methodology for the momoneric COMP-ΔN, the stoichiometry measurement for TGF-β is 0.7, which suggests a 1:1 binding ratio for the COMP monomer and TGF-β1 in the absence of manganese.

Figure 8:
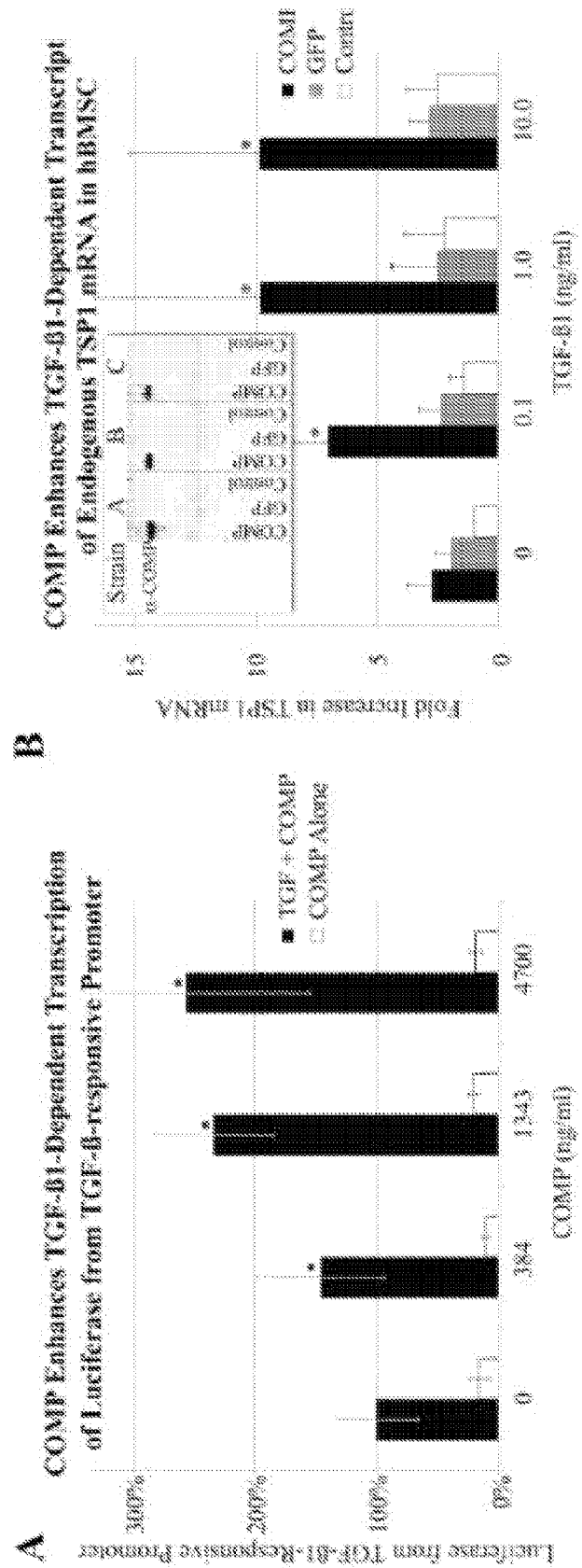
FIG. 8 A-B illustrate activation of TGF-β1-dependent transcription. A) TGF-β1-dependent transcription is enhanced in a dose-dependent manner by binding TGF-β1 to increasing amounts of COMP. A constant 4.6 ng of TGF-β1 was complexed to increasing amounts of COMP, then added to cell cultures. Transcriptional activation (luciferase activity) was normalized, with the response of 4.6 ng TGF-β1 without COMP set to 100% activity. COMP alone had no effect on TGF-β1-dependent luciferase activity. Each experiment was performed with three technical replicates. Error bars indicate the standard deviation from three independent experiments, * indicates p<0.05. B) COMP overexpression enhances TGF-β1-dependent transcription of endogenous mRNA (thrombospondin-1, TSP1) in 3 strains of human bone marrow stem cells. TSP1 expression in response to different doses of TGF-β1 was compared in cells overexpressing COMP, GFP, or untransduced control cells, using TaqMan quantitative RT-PCR. Expression of COMP increased the response to all doses of TGF-β1, while there was no statistically significant effect of GFP expression compared to untransduced cells. Graph shows average response in BMSCs isolated from 3 different donors, with error bars representing the standard deviation. * indicates significantly different from control, p<0.05 by ANOVA, and student's T-test with post-hoc corrections for multiple comparisons. COMP overexpression was confirmed by Western blot with an anti-COMP antibody (inset). COMP protein was not detected in GFP-transduced or untransduced stem cells from any of the donors.

The COMP-TGF-β1 complex enhances cellular response to TGF-β1. We wanted to determine the effect of COMP on TGF-β1-dependent transcriptional activity. Our first approach was to use an established cell line with a TGF-β-dependent luciferase reporter. We used the PAI-1/luciferase assay developed by Dr. Rifkin's laboratory, in which a TGF-β responsive promoter (PAI-1) drives the expression of firefly luciferase. This TGF-β-responsive construct was stably transfected into mink lung epithelial cells (Abe, et al., (1994) *Anal Biochem* 216, 276-284). In this system, we determined that 4.6 ng/ml of TGF-β1 consistently resulted in a mid-range luciferase response in 30 hours. To test the effect of COMP on TGF-β1-dependent transcription, we pre-incubated 4.6 ng/ml of TGF-β1 with increasing amounts of COMP, and then the TGFβ1-COMP complex was added to the cells as before. We observed that the TGF-β1-COMP complex elicited a greater transcriptional response than the same amount of unbound TGF-β1. The magnitude of the increased response was dependent on the amount of COMP used (FIG. 8a). COMP alone did not activate TGF-β-dependent transcription in this assay. These results demonstrate that COMP can enhance the cellular response to TGF-β1 in a cell line using luciferase-based measure of transcription. To confirm that COMP enhances the cellular response to TGFβ1 in primary human cells using endogenous gene activation, we tested the expression of thrombospondin-1 mRNA (TSP1), a known TGF-β response gene. COMP was overexpressed in bone marrow stem cells isolated from three individual donors, and the transcription of endogenous TSP1 was measured in response to TGF-β. Un-transduced, or GFP-transduced cells were used as a control. We found that COMP overexpression enhanced the transcriptional response to all doses of TGF-β (FIG. 8b). These cells did not express detectable levels of endogenous COMP (FIG. 8b inset). Taken together, these results demonstrate that COMP enhances the response to TGF-β, in cell lines using a luciferase reporter, and in primary cells using an endogenous TGF-β-responsive mRNA.

DISCUSSION

In this study, we demonstrate that COMP directly binds to members of the TGF-β family of growth factors including BMPs, and characterized the interaction between TGF-β1 and COMP in greater detail. The binding interaction is improved at slightly acidic conditions, and enhanced by the presence of manganese but not other cations. At least two binding sites are present on each arm of the COMP pentamer, which can both be occupied simultaneously. The binding of TGF-β to COMP has the biological effect of enhancing TGF-β-dependent transcriptional activation in the mink lung cell system.

Our study identifies a direct interaction between COMP and the active 25 kDa TGF-β ligand. A large body of existing research shows that a fundamentally different interaction exists between thrombospondin-1 and TGF-β1 (Derynck and Miyazono, 2007. "The TGF-β family." Cold Spring Harbor Laboratory Press, Cold Spring Harbor, N.Y.). Thrombospondin-1 has specific sequences in its TSP1 domain that bind the TGF-β latency associated peptide (LAP). The resulting conformational change in the latent complex then releases the active TGFβ peptide. The active TGF-β peptide itself does not interact directly with thrombospondin-1. COMP is a divergent member of the thrombospondin family, and does not contain a TSP1 domain. Furthermore, COMP does not contain the specific amino acid sequence in TSP1 that binds the LAP domain. To the best of our knowledge, COMP cannot activate latent TGF-β.

COMP is itself a transcriptional target of TGFβ signaling, both in chondrocytes and in stem cells during chondrogenesis (Recklies, et al., (1998) *Arthritis Rheum* 41, 997-1006; Barry, et al., (2001) *Exp Cell Res* 268, 189-200; and Motaung, et al, *J Tissue Eng Regen Med.* 2011 June; 5(6):e87-96). We have shown in a recently submitted manuscript that the induction of COMP by TGF-β1 occurs within 2 hours in human stem cells (Li, et al., (2011) *Osteoarthritis and cartilage/OARS, Osteoarthritis Research Society*). Furthermore, COMP is a primary response gene targeted directly by TGFβ1 signal transduction, and TGF-β1 stimulates COMP mRNA synthesis in the absence of additional protein synthesis. The observation that COMP enhances TGF-β-dependent transcription may therefore indicate a positive feedback loop for the production of COMP protein by TGF-β.

Cartilage matrix has a normal pH range of 6.6 to 6.9 (36). Synovial fluid, which has a normal pH of about 7.3, is primarily responsible for clearing the lactic acid resulting from chondrocyte glycolysis (A. Maroudas, in Sokoloff, L. (1978) *The Joints and Synovial Fluid*, Academic Press, New York). The fixed negative charges in the cartilage proteoglycans cause the extracellular pH of cartilage to be about 0.5 units below that of the synovial fluid (Simkin, et al., (1992) *J Rheumatol* 19, 1017-1019). The pH optimum for the COMP-TGF-β interaction is in the proper range for binding interactions that occur in the extracellular matrix of cartilage. In arthritic diseases the pH of cartilage is thought to be somewhat more acidic. The pH of the synovial fluid can drop to as low as 6.5 (Ohshima, et al., (1992) *Spine* (Phila Pa. 1976) 17, 1079-1082), and chondrocytes respond to the inflammatory conditions and the presence of IL-1 by increasing their production of lactic acid (Parkar, et al., (1998) *FEBS Lett* 428, 171-176). We found reduced binding of COMP to TGF-β below pH 6.75. This suggests that the interaction between these two molecules may be reduced in arthritis as a result of the acidification of the matrix, and especially the pericellular matrix. However, the effect of the reduced pH on the biological response to the COMP-TGF-β complex remains unknown.

The binding of COMP to extracellular matrix and cell-surface proteins is often dependent on the presence of divalent cations such as calcium (Chen, et al., (2000) *J Biol Chem* 275, 26538-26544), magnesium, zinc, and manganese (Di Cesare, et al., (2002) *Matrix Biol* 21, 461-470). EDTA changes the conformation of COMP, which alters its binding properties and increases its susceptibility to proteolytic degradation. In fact, the first step in purification of native COMP from cartilage is the extraction of COMP with EDTA in the presence of proteinase inhibitors (Di Cesare, et al, (1996) *J Orthop Res* 14, 946-955). The recombinant COMP used in our experiments was synthesized and purified in the presence of calcium and magnesium. Given the large effect of cations on the conformation and binding properties of COMP, we were somewhat surprised to find that the binding of COMP to TGF-β was not affected by additional calcium or by chelation of calcium with EDTA. Of the cations tested, only manganese increased the extent of interaction between COMP and TGF-β1. Manganese also enhances the interaction between COMP and fibronectin fragments (Di Cesare, et al., (2002) *Matrix Biol* 21, 461-470). Together, these observations suggest that manganese causes a conformational molecular change in the COMP molecule that is required for the additional binding site to TGF-β1.

Genetic mutations of the COMP gene lead to protein misfolding and retention in the endoplasmic reticulum. The resulting chondrocyte apoptosis is the basis for pseudoachondroplasia and multiple epiphyseal dysplasia (Briggs, et al., (1995) *Nature* 10, 330-336; Hecht, et al., (1995) *Nat Genet* 10, 325-329). A COMP knockout mouse is viable with no obvious phenotype, although closer inspection revealed disturbances in the growth plate (Posey, et al., (2008) *Am J Pathol* 172, 1664-1674), and the knockout mice are somewhat more prone to develop arthritis. Whether this is due to impaired mechanical properties of cartilage matrix assembled in the absence of COMP, or to altered TGF-β-dependent pathways in cartilage without COMP remains to be determined.

We measured an intermediate binding affinity between COMP and TGF-β1. The estimated dissociation constants were in the nM range from both DPI and ELISA solid phase binding experiments. This is in agreement with the affinity of COMP to other matrix proteins, such as fibronectin (Di Cesare, et al., (2002) *Matrix Biol* 21, 461-470) and matrilin-4 (Mann, et al., *J Biol Chem*. (2004) 279(24):25294-8). However, this is at least an order of magnitude weaker than the binding of TGF-β1 with its type I, II, and III receptors, which have dissociation constants in the range of 50-300 pM (Lin, et al., (1995) *J Biol Chem* 270, 2747-2754).

Figure 9:
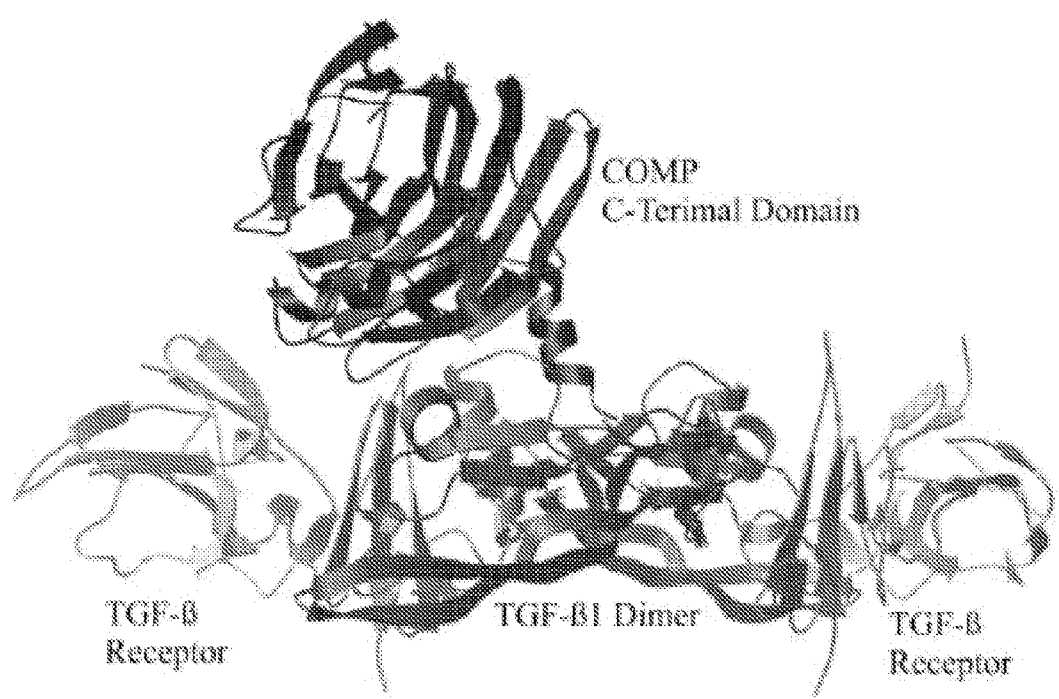
FIG. 9 illustrates docking simulation of the COMP-TGF-β1 interaction. A model of the COMP-TGF-β/receptor interaction as predicted by AutoDock3 software. The model with the lowest docking energy (−18.24 kcal/mol) is shown. A single C-terminal domain of COMP (in dark blue) is predicted to bind to the TGF-β1 dimer (in green/red) in a manner that permits the interaction of the growth factor with its receptor complex (cyan, pink and gold). According to this model, a mechanism through which pentameric COMP enhances TGF-β-dependent signaling by clustering multiple TGF-β1 and receptors at the cell surface.
Figure 11:
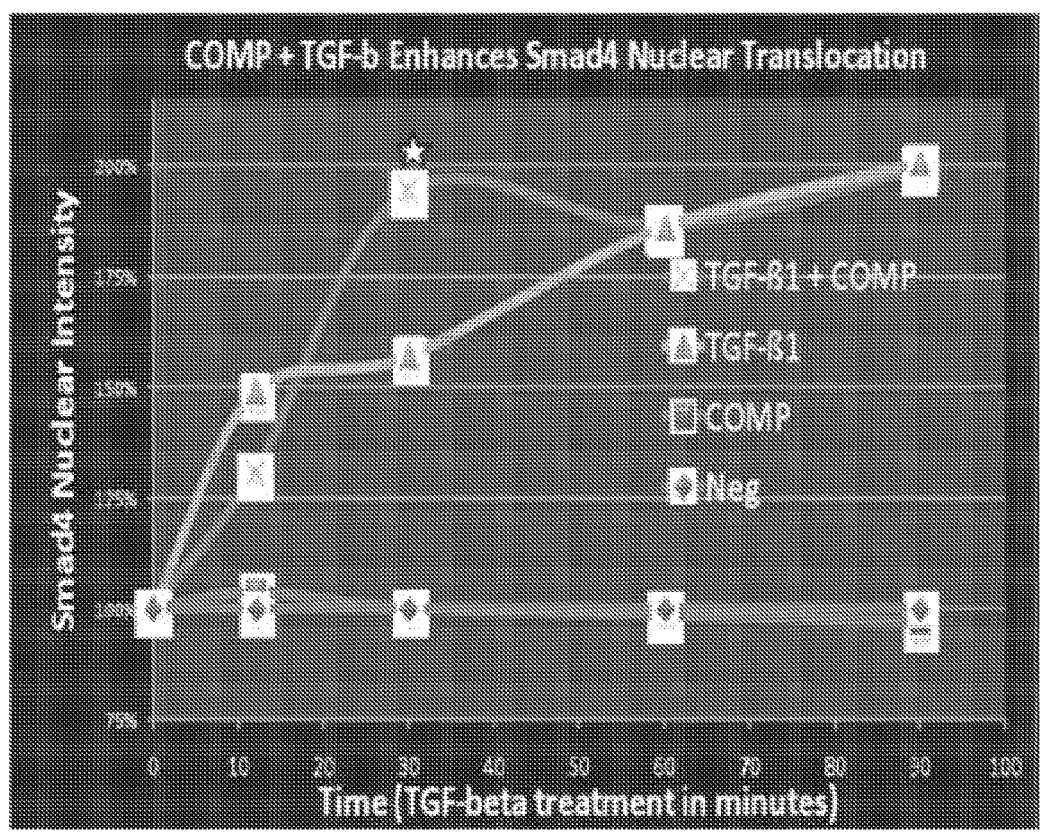
FIG. 11 illustrates that the COMP+TGF-β1 complex enhances the chondrocyte response to TGF-β1. Increased nuclear translocation of Smad4 is observed in the presence of COMP+TGF-β1, when compared to unbound TGF-β1. COMP alone had no effect on Smad4 nuclear translocation. Chondrocytes were treated with TGF-β1, COMP, or pre-bound COMP+TGF-β1. Immunofluorescence microscopy of Smad4 was performed, with DAPI to stain the nuclei. Approximately 1800 cells were imaged (~90 for each point on the graph) and analyzed for colocalization of Smad4 with DAPI. Statistical analysis was ANOVA with Tukey's posthoc correction for multiple comparisons, on JMP software. * indicates statistically different between COMP and TGF-β1+ COMP.
Figure 12:
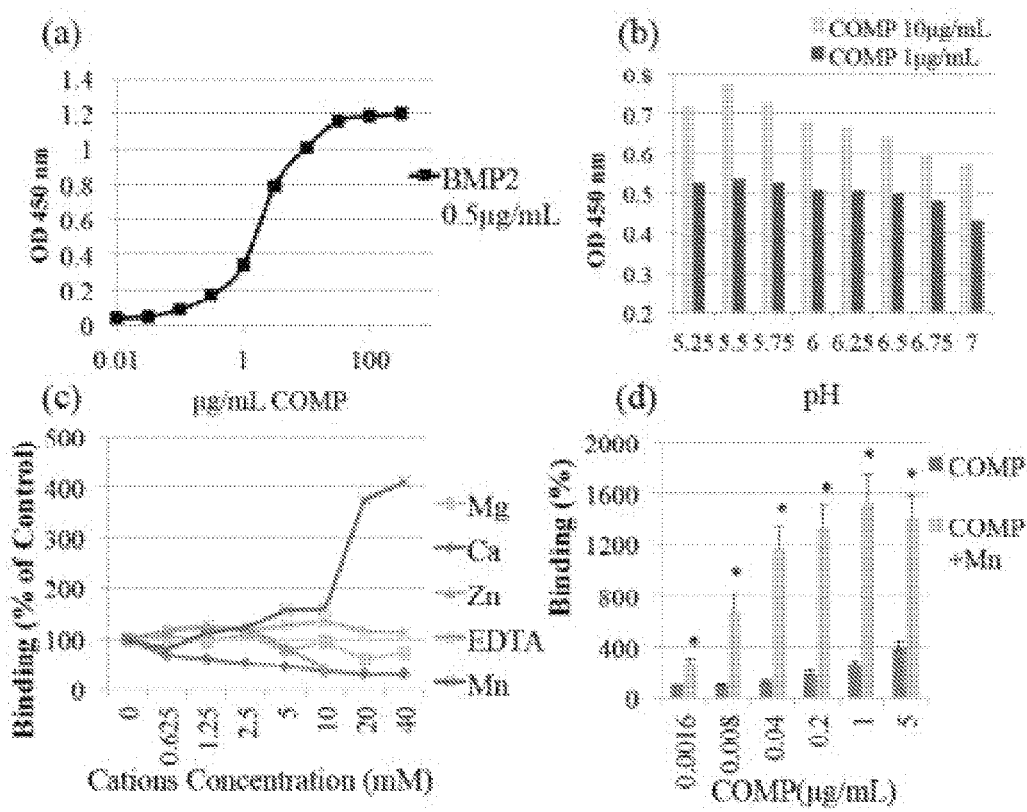
FIG. 12 A-D illustrate that COMP binds BMP2: A) COMP binds to BMP2 in a dose-dependent manner as measured by solid-phase ELISA assay. B) COMP binds to BMP2 at a slightly acidic pH, with an optimum binding observed between pH 5.50 and pH 5.75. Binding below pH 5.25, or above pH 7.3, was not tested. C) Binding between COMP and BMP2 is strongly enhanced by manganese, while only minor effects are seen in the presence of calcium, zinc, magnesium, or EDTA. D) Manganese enhances the affinity of COMP to BMP2.
Figure 13:
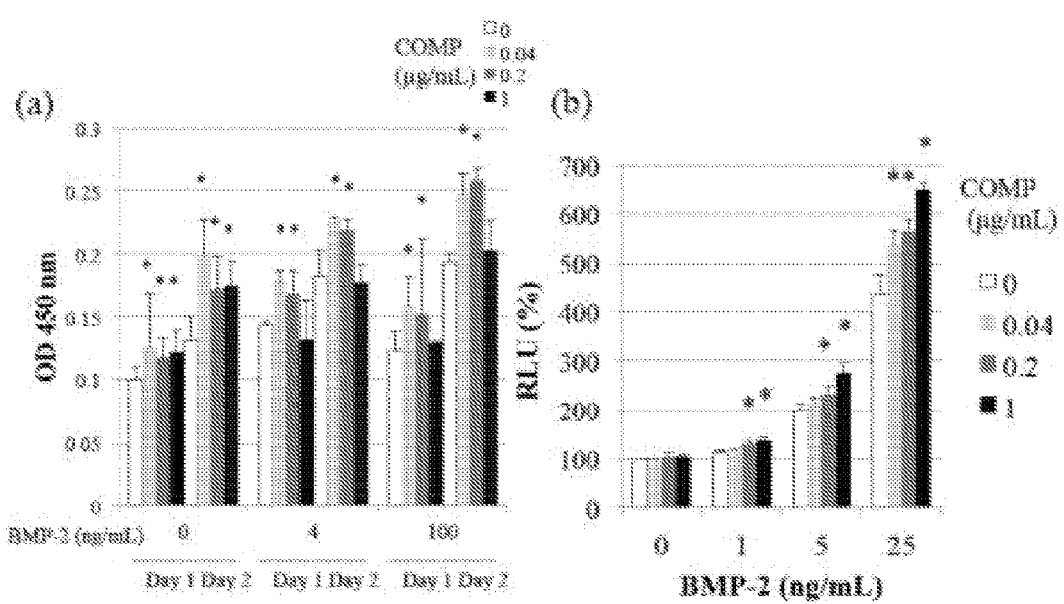
FIG. 13 A-B illustrate that COMP enhances BMP2 activity. A) COMP enhances BMP2-dependent increase in proliferation. BMP2 alone causes increased proliferation of mouse C2C12 myoblasts, as measured by the WST assay for mitochondrial activity. COMP enhances the increase in proliferation caused by BMP2. B) COMP enhances BMP2-dependent transcriptional activation of a BMP-response gene promoter driving the expression of luciferase. We observed a dose-dependent effect of COMP on BMP2.
Figure 14:
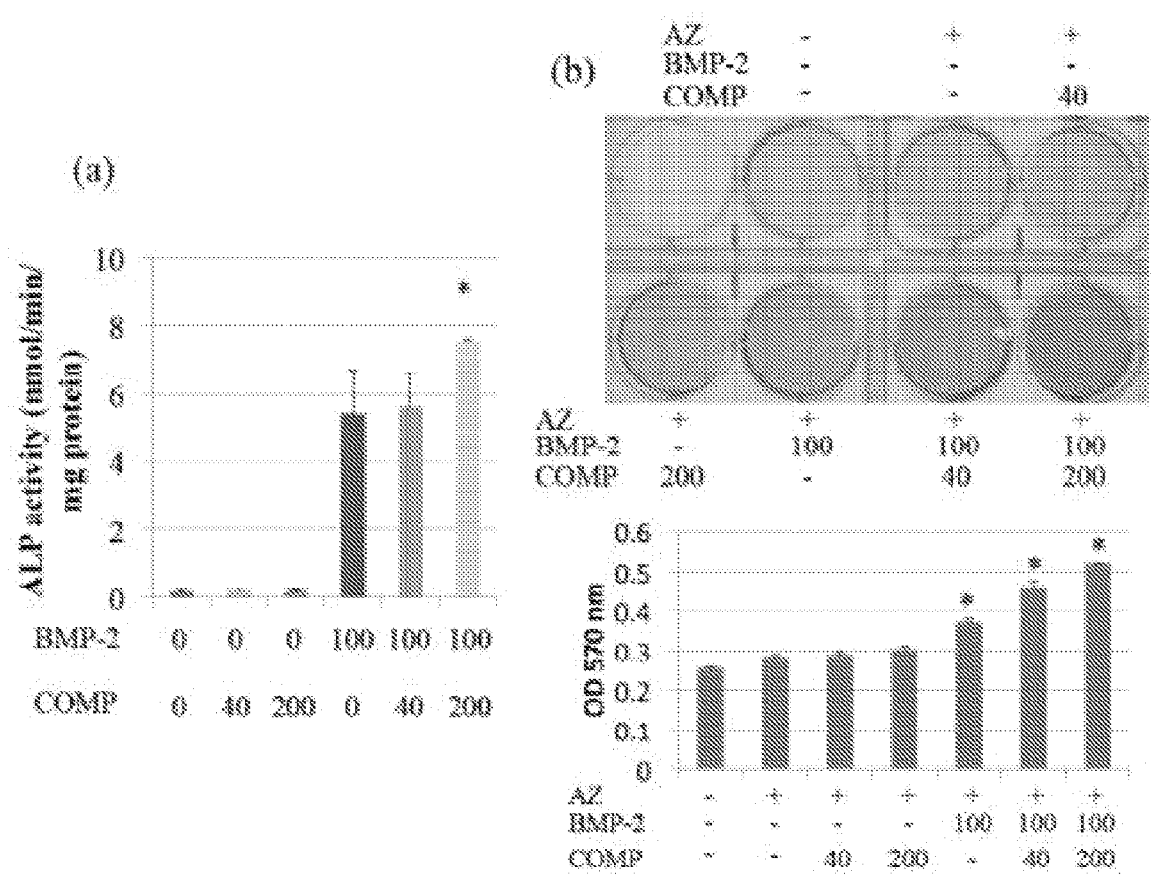
FIG. 14 A-B illustrate that COMP enhances BMP2-dependent osteogenesis: A) BMP-dependent increase in alkaline phosphatase activity, an established assay for in-vitro osteogenesis, is enhanced by COMP. B) COMP enhances BMP2-dependent matrix mineralization, as measured by alizarin red staining. Top panel shows alizarin red stain in representative tissue culture dishes. Bottom panel shows average quantified stain in replicate wells. For both assays, C2C12 cells were cultured in vitro using osteogenic media supplemented with BMP, COMP, or both, in the concentrations given.
Figure 15:
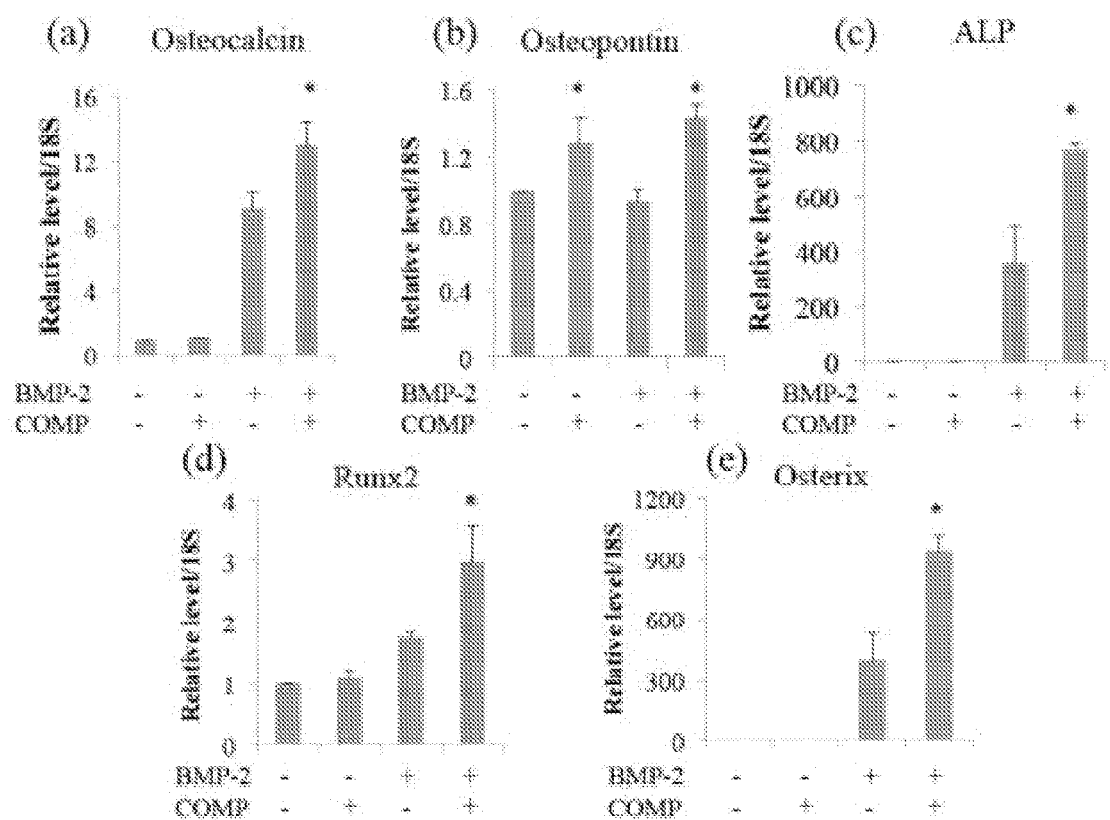
FIG. 15 A-E illustrate that COMP enhances BMP2-dependent expression of osteogenic genes: BMP2-dependent osteogenic gene expression was measured by TaqMan quantitative RT-PCR, for Osteocalcin (a), Osteopontin (b), Alkaline phosphatase (c), Runx2 (d) and Osterix (e). In every case, BMP2 activity was enhanced by COMP, while COMP itself had little or no effect on the gene expression. Assays were performed in C2C12 cells, grown in osteogenic culture medium.
Figure 16:
FIG. 16 illustrates that COMP extends BMP Receptor levels in the presence of BMP2 ligand. Once bound to BMP ligands, the BMP receptor complex is internalized by the cell, and then either degraded or recycled. The Western blot shows reduced degradation of BMP receptor when BMP2 ligand is added in the presence of COMP (lane 4) compared to when BMP2 ligand is added alone (lane 2). COMP itself has little effect (lane 3) compared to control (lane 1). This extends the time that the BMP2 signaling pathway is activated, and provides one explanation for how COMP enhances BMP activity.
Figure 17:
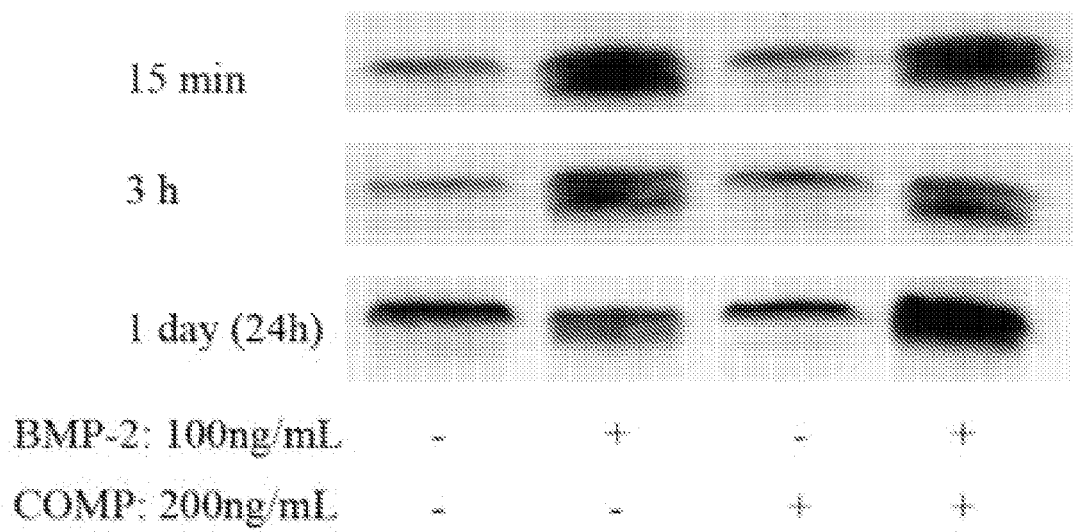
FIG. 17 illustrates that COMP extends BMP-dependent pathway activation. Phosphorylation of Smad1/5/8 proteins indicates activation of the BMP-dependent signal transduction pathway. In the presence of COMP, BMP2-dependent Smad1/5/8 phosphorylation is enhanced at 24 hours, but when BMP2 alone is added, Smad1/5/8 phosphorylation returns to baseline at 24 hours. Again, this enhanced activation of the BMP signaling pathway provides one explanation COMP enhances BMP activity.

Insight into how COMP may enhance TGF-β signaling is gained from molecular docking simulations performed with the crystal structures of COMP and TGF-β and its receptors (FIG. 9). This model suggests that a single c-terminal domain of COMP can be bound to the TGF-β active dimer, and form a complex with the TGF-β receptors. According to this model, a mechanism through which pentameric COMP enhances TGF-β signaling would be to increase the clustering of the TGF-β-receptors.

The biological effect of the TGF-β-COMP interaction is to enhance the cellular response to TGF-β. The same amount of TGF-β1 elicited a much greater transcriptional response when precomplexed to COMP than when presented as free growth factor. Presented in a different way, in the presence of COMP, the amount of TGF-β1 required to elicit maximal transcriptional activation could be reduced by at least 50-fold.

In conclusion, COMP bound to all of the TGFβ-family of ligands we tested. In the case of TGFβ1, this interaction enhanced the biological response to TGF-β1. Our working model is that a COMP pentamer binds to multiple TGF-β ligands and presents these to cell surface receptors. These data provide a new insight into the function of COMP in cartilage and bone biology.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

```
                         INFORMAL SEQUENCE LISTING

SEQ ID NO: 1 - full-length human COMP monomer (GenBank Refs:
NP_000086.2 GI: 40217843)
    1 mvpdtacvll ltlaalgasg qgqsplgsdl gpqmlrelqe tnaalqdvre llrqqvreit
   61 flkntvmecd acgmqqsvrt glpsvrpllh capgfcfpgv aciqtesgar cgpcpagftg
  121 ngshctdvne cnahpcfprv rcintspgfr ceacppgysg pthqgvglaf akankqvctd
  181 inecetgqhn cvpnsvcint rgsfqcgpcq pgfvgdqasg cqrraqrfcp dgspsecheh
  241 adcvlerdgs rscvcavgwa gngilcgrdt dldgfpdekl rcperqcrkd ncvtvpnsgq
  301 edvdrdgigd acdpdadgdg vpnekdncpl vrnpdqrntd edkwgdacdn crsqknddqk
  361 dtdqdgrgda cdddidgdri rnqadncprv pnsdqkdsdg dgigdacdnc pqksnpdqad
  421 vdhdfvgdac dsdqdqdgdg hqdsrdncpt vpnsaqedsd hdgqgdacdd dddndgvpds
  481 rdncrlvpnp gqedadrdgv gdvcqddfda dkvvdkidvc penaevtltd frafqtvvld
  541 pegdaqidpn wvvlnqgrei vqtmnsdpgl avgytafngv dfegtfhvnt vtdddyagfi
  601 fgyqdsssfy vvmwkqmeqt ywqanpfrav aepgiqlkav ksstgpgeql rnalwhtgdt
  661 esqvrllwkd prnvgwkdkk syrwflqhrp qvgyirvrfy egpelvadsn vvldttmrgg
  721 rlgvfcfsqe niiwanlryr cndtipedye thqlrqa SEQ ID NO: 2 - COMP[pfam11598] domain consensus:
    1 DCAKQLARQLSELTQLLQELREDLRQQVKETAFLRNTIEECQACG                45

SEQ ID NO: 3 - COMP[pfam11598] domain within human COMP
monomer, positions 29-73:
   29 DLGPQMLRELQETNAALQDVRELLRQQVREITFLKNTVMECDACG                73
```

-continued

INFORMAL SEQUENCE LISTING

SEQ ID NO: 4 - EGF_CA[pfam07645] domain consensus:
  1 DVDECADGTHNCPANTVCVNTIGSFEC-VCPDGY                                    33

SEQ ID NO: 5 - EGF_CA[pfam07645] domain within human COMP
monomer, positions 180-213:
  180 DINECETGQHNCVPNSVCINTRGSFQCgPCQPGF                                  213

SEQ ID NO: 6 - EGF_CA[cd00054] domain consensus
  1 DIDECASG-NPCQNGGTCVNTVGSYRCS-CPPGYTGR                                 35

SEQ ID NO: 7 - EGF_CA[cd00054] domain within human COMP
monomer, positions 180-216:
  180 DINECETGqHNCVPNSVCINTRGSFQCGpCQPGFVGD                               216

SEQ ID NO: 8 - EGF_CA[smart00179] domain consensus
  1 DIDECaSGNPCQNGGTCVNTVGSYRCE-CPPGYTDGRN                                37

SEQ ID NO: 9 - EGF_CA[smart00179] domain within human COMP
monomer, positions 127-163:
  127 DVNEC-NAHPCFPRVRCINTSPGFRCEaCPPGYSGPTH                              163

SEQ ID NO: 10 - TSP_C[pfam05735] domain consensus
QIDPNWVVYNQGAEIVQTLNSDPGLAVGYDAFEGVDFEGTFFINTTTDDDYVGFVFGYQSN
SKFYVVMWKKAEQTYWQANPFRASAEPGIQLKLVNSTTGPGEALRNALWHTGDTTNQVRLL
WKDPRNIGWKPRTAYRWQLHHRPSIGYIRVRMYEGNHLVADSGNIYDSTLRGGRLGVFCFS
QEMIIWSNLKYRCNDTIP SEQ ID NO: 11 - TSP_C[pfam05735] domain within human COMP
monomer, positions 546-746
QIDPNWVVLNQGREIVQTMNSDPGLAVGYTAFNGVDFEGTFHVNTVTDDDYAGFIFGYQDS
SSFYVVMWKQMEQTYWQANPFRAVAEPGIQLKAVKSSTGPGEQLRNALWHTGDTESQVRLL
WKDPRNVGWKDKKSYRWFLQHRPQVGYIRVRFYEGPELVADSNVVLDTTMRGGRLGVFCFS
QENIIWANLRYRCNDTIP SEQ ID NO: 12 - C-terminal COMP domain
AVAEPGIQLKAVKSSTGPGEQLRNALWHTGDTESQVRLLWKDPRNVGWKDKKSYRWFLQHR
PQVGYIRVRFYEGPELVADSNVVLDTTMRGGRLGVFCFSQENIIWANLRYRCNDTIPEDYE
THQLRQA SEQ ID NO: 13 -COMP monomer residues 527-757
TLTDFRAFQTVVLDPEGDAQIDPNWVVLNQGREIVQTMNSDPGLAVGYTAFNGVDFEGTFH
VNTVTDDDYAGFIFGYQDSSSFYVVMWKQMEQTYWQANPFRAVAEPGIQLKAVKSSTGPGE
QLRNALWHTGDTESQVRLLWKDPRNVGWKDKKSYRWFLQHRPQVGYIRVRFYEGPELVADS
NVVLDTTMRGGRLGVFCFSQENIIWANLRYRCNDTIPEDYETHQLR

What is claimed is:

1. An isolated protein complex comprising one or more monomers of cartilage oligomeric matrix protein (COMP) bound to one or more growth factors, wherein the one or more monomers of COMP comprise a growth factor binding domain, and wherein at least one of the growth factors is a member of the transforming growth factor-beta (TGF-β) superfamily.

2. The protein complex of claim 1, wherein the complex comprises five monomers of COMP.

3. The protein complex of claim 1, wherein the monomers of COMP comprise one or more domains selected from the group consisting of a thrombospondin-3 (TSP-3) domain and a COMP domain.

4. The protein complex of claim 1, wherein the monomers of COMP do not comprise one or more domains selected from the group consisting of an N-terminal oligomerization domain and an epidermal growth factor (EGF)-like domain.

5. The protein complex of claim 1, wherein the monomers of COMP comprise one or more domains selected from the group consisting of an N-terminal oligomerization domain and an epidermal growth factor (EGF)-like domain.

6. The protein complex of claim 1, wherein at least two growth factor polypeptides are bound to one COMP monomer.

7. The protein complex of claim 1, wherein the one or more growth factors are selected from the group consisting of TGF-β1, TGF-β2, TGF-β3, bone morphogenetic protein (BMP)-2, BMP-3, BMP-4, BMP-5, BMP-6 and BMP-7.

8. The protein complex of claim 1, wherein the one or more growth factors are selected from the group consisting of TGF-β1, TGF-β2, TGF-β3, BMP-2, BMP-3, BMP-4, BMP-5, BMP-6, BMP-7, fibroblast growth factor-2 (FGF-2), hepatic growth factor (HGF), vascular endothelial growth factor (VEGF) and insulin-like growth factor 1 (IGF-1).

9. A protein scaffold comprised of an isolated COMP pentamer bound to one or more growth factors, wherein the COMP pentamer is comprised of five COMP monomers, and wherein at least one of the growth factors is a member of the transforming growth factor-beta (TGF-β) superfamily.

10. The protein scaffold of claim 9, wherein the monomers of COMP do not comprise one or more domains selected from the group consisting of an N-terminal oligomerization domain and an epidermal growth factor (EGF)-like domain.

11. The protein scaffold of claim 9, wherein the monomers of COMP comprise one or more domains selected from the group consisting of an N-terminal oligomerization domain and an epidermal growth factor (EGF)-like domain.

12. The protein scaffold of claim 9, wherein the one or more growth factors are selected from the group consisting of TGF-β1, TGF-β2, TGF-β3, BMP-2, BMP-3, BMP-4, BMP-5, BMP-6, and BMP-7.

13. The protein scaffold of claim 9, wherein the one or more growth factors are selected from the group consisting of TGF-β1, TGF-β2, TGF-β3, BMP-2, BMP-3, BMP-4, BMP-5, BMP-6, BMP-7, fibroblast growth factor-2 (FGF-2), hepatic growth factor (HGF), vascular endothelial growth factor (VEGF) and insulin-like growth factor 1 (IGF-1).

14. A matrix comprising a protein complex of claim 1.

15. The matrix of claim 14, wherein the matrix is bioresorbable or biodegradable.

16. The matrix of claim 14, wherein the matrix is configured as a sheet or as a bone graft.

17. The matrix of claim 14, wherein the matrix further comprises one or more materials selected from the group consisting of treated cartilage and bone matrices, collagens, hyaluronan, fibrin gels, carbon fibers, porous polylactic acid, type I collagen gel, and type II collagen gel.

18. The matrix of claim 14, wherein the matrix further comprises one or more bone matrix proteins selected from the group consisting of, osteocalcin, osteonectin, bone sialoprotein (BSP), lysyloxidase, cathepsin L pre, osteopontin, matrix GLA protein (MGP), biglycan, decorin, proteoglycan-chondroitin sulfate III (PG-CS III), bone acidic glycoprotein (BAG-75), thrombospondin (TSP) and fibronectin.

19. The protein scaffold of claim 9, wherein at least two growth factor polypeptides are bound to one COMP pentamer.

20. A method for repairing a cartilage lesion, comprising implanting into the cartilage lesion a protein complex of claim 1, wherein protein complex promotes chondrogenesis, thereby repairing the cartilage lesion.

21. The method of claim 20, wherein the cartilage lesion is an articular cartilage lesion.

22. The method of claim 20, wherein the cartilage lesion is a meniscal cartilage lesion.

23. The method of claim 20, wherein the growth factor is TGF-β1.

24. A method of promoting bone growth at a bone lesion, comprising contacting the bone lesion with a protein complex of claim 1 wherein the protein complex promotes bone growth at the bone lesion.

25. The method of claim 24, wherein the bone lesion is a bone fracture.

26. The method of claim 24, wherein the bone lesion is a spinal fusion site.

27. The method of claim 24, wherein the one or more growth factors are selected from the group consisting of BMP-2, BMP-3, BMP-4, BMP-5, BMP-6 and BMP-7.

28. A method of promoting chondrogenesis, comprising contacting a cell capable of producing cartilage with a protein complex of claim 1.

29. The method of claim 28, wherein the cell is a chondrocyte.

30. The method of claim 28, wherein the cell is a stem cell.

31. The method of claim 28, wherein the cell capable of producing cartilage is in vivo.

32. The method of claim 28, wherein the cell capable of producing cartilage is in vitro.

33. The method of claim 28, wherein the growth factor is TGF-β1.

34. A method of promoting osteogenesis, comprising contacting a cell capable of producing bone with a protein complex of claim 1.

35. The method of claim 34, wherein the cell is an osteoblast.

36. The method of claim 34, wherein the cell is a stem cell.

37. The method of claim 34, wherein the cell capable of producing bone is in vivo.

38. The method of claim 34, wherein the cell capable of producing bone is in vitro.

39. The method of claim 34, wherein the one or more growth factors are selected from the group consisting of BMP-2, BMP-3, BMP-4, BMP-5, BMP-6 and BMP-7.

40. A method of delivering one or more growth factors to a target cell, comprising contacting the target cell with a protein complex of claim 1.

41. The method of claim 40, wherein the target cell is a chondrocyte.

42. The method of claim 40, wherein the target cell is an osteoblast.

43. The method of claim 40, wherein the target cell is in a subject and the protein complex or protein scaffold is administered to the subject.

* * * * *